United States Patent
Boggs, II et al.

(10) Patent No.: US 11,883,660 B2
(45) Date of Patent: *Jan. 30, 2024

(54) ELECTRICAL STIMULATOR FOR PERIPHERAL STIMULATION

(71) Applicant: SPR Therapeutics, Inc., Cleveland, OH (US)

(72) Inventors: Joseph W. Boggs, II, Chapel Hill, NC (US); Robert B. Strother, Willoughby Hills, OH (US); Kathryn W. Stager, University Heights, OH (US); Jonathan L. Sakai, Fairview Park, OH (US); Amorn Wongsarnpigoon, Chapel Hill, NC (US); Matthew deBock, Morrisville, NC (US); Devin Sell, Brecksville, OH (US); Meredith McGee, Cary, NC (US)

(73) Assignee: SPR Therapeutics, Inc., Cleveland, OH (US)

( * ) Notice: Subject to any disclaimer, the term of this patent is extended or adjusted under 35 U.S.C. 154(b) by 206 days.

This patent is subject to a terminal disclaimer.

(21) Appl. No.: 17/233,642

(22) Filed: Apr. 19, 2021

(65) Prior Publication Data

US 2021/0252286 A1 Aug. 19, 2021

Related U.S. Application Data

(63) Continuation of application No. 15/822,768, filed on Nov. 27, 2017, now Pat. No. 10,981,005, which is a
(Continued)

(51) Int. Cl.
*A61N 1/00* (2006.01)
*A61N 1/36* (2006.01)
(Continued)

(52) U.S. Cl.
CPC .......... *A61N 1/36017* (2013.01); *A61N 1/05* (2013.01); *A61N 1/0502* (2013.01);
(Continued)

(58) Field of Classification Search
CPC ............ A61N 1/36017; A61N 1/36021; A61N 1/375; A61N 1/05; A61N 1/0502;
(Continued)

(56) References Cited

U.S. PATENT DOCUMENTS

| | | |
|---|---|---|
| 6,845,271 B2 | 1/2005 | Fang et al. |
| 7,376,467 B2 | 5/2008 | Thrope et al. |

(Continued)

FOREIGN PATENT DOCUMENTS

WO 2013/162708 A2 10/2013

OTHER PUBLICATIONS

Patent Cooperation Treaty (PCT), International Search Report and Written Opinion for Application PCT/US2015/062828 filed Nov. 27, 2015, dated Feb. 18, 2016, 12 pgs., International Searching Authority, European Patent Office, NL.

*Primary Examiner* — Scott M. Getzow
(74) *Attorney, Agent, or Firm* — McDonald Hopkins LLC

(57) ABSTRACT

Neurostimulation assemblies, systems, and methods make possible the providing of short-term therapy or diagnostic testing by providing electrical connections between muscles and/or nerves inside the body and stimulus generators and/or recording instruments mounted on the surface of the skin or carried outside the body. The assembly affords maximum patient mobility and comfort through differentiated components having minimal profiles and connected by way of detachable and adjustable connections.

22 Claims, 22 Drawing Sheets

Related U.S. Application Data continuation of application No. 14/953,099, filed on Nov. 27, 2015, now Pat. No. 9,827,419.

(60) Provisional application No. 62/084,744, filed on Nov. 26, 2014.

(51) Int. Cl.
| | | |
|---|---|---|
| *A61N 1/05* | (2006.01) | |
| *A61N 1/375* | (2006.01) | |
| *H01R 11/30* | (2006.01) | |
| *H01R 13/20* | (2006.01) | |
| *G01R 31/68* | (2020.01) | |

(52) U.S. Cl.
CPC .... *A61N 1/36021* (2013.01); *A61B 2562/227* (2013.01); *A61N 1/0551* (2013.01); *A61N 1/3752* (2013.01); *G01R 31/68* (2020.01); *H01R 11/30* (2013.01); *H01R 13/20* (2013.01); *H01R 2201/12* (2013.01)

(58) Field of Classification Search
CPC .... A61N 1/3752; A61N 1/0551; H01R 13/20; H01R 11/30; H01R 2201/12; G01R 31/043; A61B 2562/227
See application file for complete search history.

(56) References Cited

U.S. PATENT DOCUMENTS

| | | | |
|---|---|---|---|
| 7,483,747 | B2 | 1/2009 | Gliner et al. |
| 8,249,713 | B2 | 8/2012 | Fang et al. |
| 8,463,383 | B2 | 6/2013 | Sakai et al. |
| 8,626,302 | B2 | 1/2014 | Bennett et al. |
| 8,700,177 | B2 | 4/2014 | Strother et al. |
| 8,954,153 | B2 | 2/2015 | Boggs, II |
| 2003/0077935 | A1 | 4/2003 | Stein et al. |
| 2003/0199948 | A1 | 10/2003 | Kokones et al. |
| 2010/0048062 | A1 | 2/2010 | Cappa et al. |
| 2012/0143062 | A1 | 6/2012 | Nordgren et al. |
| 2012/0200331 | A1 | 8/2012 | Karlsson et al. |
| 2012/0203314 | A1 | 8/2012 | Deininger et al. |
| 2012/0245514 | A1 | 9/2012 | Joglekar |
| 2014/0046416 | A1 | 2/2014 | Bennett et al. |
| 2014/0200640 | A1 | 7/2014 | Wulfman et al. |
| 2014/0296938 | A1 | 10/2014 | Kothandaraman et al. |
| 2014/0371802 | A1 | 12/2014 | Mashicah et al. |
| 2015/0025609 | A1 | 1/2015 | Govea |
| 2015/0311621 | A1 | 10/2015 | Carley et al. |
| 2016/0250466 | A1 | 9/2016 | Boggs et al. |

ELECTRICAL STIMULATOR FOR PERIPHERAL STIMULATION

CROSS REFERENCE TO RELATED APPLICATIONS

This application is a continuation of U.S. Utility application Ser. No. 15/822,768 filed on Nov. 27, 2017, which is a continuation of U.S. Utility application Ser. No. 14/953,099 filed on Nov. 27, 2015, now U.S. Pat. No. 9,827,419, which claims priority to U.S. Patent Application Ser. No. 62/084,744 filed on Nov. 26, 2014. The disclosure of these applications, along with any other United States Patents and United States Patent Publications identified in this specification, are hereby incorporated by reference.

FIELD OF USE

The present disclosure generally relates to an electrical stimulator and, more particularly, a mobile, electrical stimulator system for peripheral electrical stimulation.

BACKGROUND

Neurostimulation and brain stimulation can provide functional and/or therapeutic outcomes. While existing systems and methods provide benefits to individuals requiring neurostimulation, many quality of life issues still remain. For example, existing systems are performed solely in a clinical setting under the supervision of a clinician limiting the applicable uses and the time available for stimulation. Furthermore, the controllers utilized in these clinical settings, by today's standards, are relatively large and awkward to manipulate and transport.

There exist both external and implantable devices for providing neurostimulation in diverse therapeutic and functional restoration indications. These neurostimulators are able to provide treatment therapy to individual portions of the body. The operation of these devices typically includes use of an electrode placed either on the external surface of the skin and/or a surgically implanted electrode. In the case of external neurostimulators, surface electrodes and/or percutaneous lead(s) having one or more electrodes are used to deliver electrical stimulation to select portion(s) of the patient's body.

For example, transcutaneous electrical nerve stimulation ("TENS") is delivered through electrodes placed on the skin surface, but has not achieved widespread use due to discomfort of the therapy, muscle fatigue, and the limited efficacy. TENS is similar to electrical muscle stimulation, although the latter is intended for stimulating muscles rather than nerves.

Several clinical and technical issues associated with surface electrical stimulation have prevented it from becoming a widely accepted treatment method. First, stimulation of cutaneous pain receptors cannot be avoided resulting in stimulation-induced pain that limits patient tolerance and compliance. Second, electrical stimulation is delivered at a relatively high frequency to prevent stimulation-induced pain, which leads to early onset of muscle fatigue. Third, it is difficult to stimulate deep nerves with surface electrodes without stimulating overlying, more superficial nerves resulting in unwanted stimulation. Further still, clinical skill and intensive patient training is required to place surface electrodes reliably on a daily basis and adjust stimulation parameters to provide optimal treatment. The required daily maintenance and adjustment of a surface electrical stimulation system is a major burden on both patient and caregiver.

A number of previous systems for spinal cord stimulation (e.g., at the dorsal root ganglion) and/or other deep tissue stimulation require surgical implantation of electrodes and/or other devices for delivering the therapy. These therapies necessarily incur the cost and medical risks associated with invasive surgical procedures, and they may restrict the mobility of the patient, both in terms of the surgical procedure itself and, in some cases, in the post-operative activities an ambulatory patient may wish to engage in while in his or her home environment.

Moreover, many previous stimulation systems require complex engagement systems to operatively attach a lead with a stimulator. These systems often require separate tools to operatively attach the lead with the stimulator, require more than one person to accomplish, or are difficult to operatively attach. Often a connector is utilized to operatively attach the lead with the stimulator. These connectors are often uncomfortable for the patient to wear, require significant dexterity from the clinician to attach and/or require additional tools to attach.

U.S. Pat. Nos. 6,845,271 and 8,249,713 describe methods of treating shoulder dysfunction by way of percutaneous, electrical stimulation. Specific, asynchronous stimulation profiles are delivered via a plurality of spiral or helix wire electrodes with terminal barbs inserted into the targeted muscles. The electrodes may be inserted by a hypodermic needle or surgical procedure.

U.S. Pat. No. 7,376,467 discloses a neuromuscular stimulation assembly including a steerable introducer defining an interior lumen that shields the electrode from contact with tissue during insertion. Electrodes suitable for this assembly may be transcutaneous or percutaneous. The assembly includes a carrier, adhesively held to the patient, having an electronics pod for generating the desired electrical current patterns and an optional power input bay to enable changing the batteries for the assembly. Electrical connections between the electrodes and the power source are established via troughs that are integrally formed on the pod.

U.S. Pat. No. 8,463,383 contemplates neurostimulation assemblies for short-term therapy or diagnostic testing via a fine wire electrode. The assembly includes a carrier and an optionally removable electronics pod associated with that carrier. The pod generates the stimulating pulses and includes user interface components. A power source and optional memory unit are contained within the assembly and, more specifically, possibly within the return electrode itself.

U.S. Pat. Nos. 8,626,302 and 8,954,153 and United States Patent Publication 2013/0238066 disclose methods of alleviating pain via percutaneous and/or peripheral nerve electrical stimulation. As with other methods noted above, a hypodermic needle and lumen combination may deliver the lead. Various stimulation parameters are disclosed therein.

U.S. Pat. No. 8,700,177 describes a system and method involving the use of an adhesive patch with a mounting structure directly mated to an electrical stimulation device. A percutaneous electrode is electrically coupled to the stimulation device. The device has a low profile and may be controlled wirelessly or by way of a plugged connection. A rechargeable battery powers the device, which may be inductively charged.

SUMMARY

A compact, mobile system for peripheral electrical nerve stimulation is disclosed. This system allows for the targeted delivery of stimulation while bypassing cutaneous pain receptors and without the need for open or invasive surgical procedures. The system allows for a relatively wide range of possible pulse profiles, while reducing the risk of muscle fatigue and minimizing the need for patients to rely on skilled personnel to maintain or monitor the system.

One particularly relevant aspect of the system is that it includes one or more "breakaway" connections to ensure that the electrode and/or lead does not become dislodged in the event of inadvertent or unwanted forces being applied to the lead or its connections, e.g., application of a predefined force causes the patient cable (or lead) to break away from the stimulator. These breakaway connections may fully disconnect and/or simply reduce the tension of the connections to ensure that the electrode is unaffected. Further, the system can provide an alert to the user in the event of disconnection or reduction in tension so that the user can confirm the system is still in operational. These features, whether considered singly or in combination, prevent the user from being confined to a clinician's office (or other restricted movement/access areas) during the treatment and, instead, allow the user to engage in everyday activities.

The system is easier to use for the patient and allows the clinician to affix it to the patient. The system does not require tools to operatively attach the lead with the stimulator. Further still the system may allow a clinician to only use a single hand to operatively connect the system together.

Another aspect of the system is that it may be lightweight, has a generally low profile and is adaptable. In particular, after the electrode is positioned within the body, the combination of the adhesive bandage, the lead connector and the patient cable may allow the user to adjustably position the stimulator pod in a convenient position on his or her body. The lead connector and other system elements may be augmented to accommodate multiple electrodes, thereby enabling coordinated therapies across regions of the body. The system elements may be wirelessly connected to minimize physical connections and maximize user comfort.

Additionally, the stimulator pod and controller pod may be further augmented through use of a programmer unit during the treatment, so that the clinician or even the user can directly control the process.

As noted above, the breakaway feature may permit disconnection of the patient cable from the stimulator pod when a predefined force is applied. The system on the body may maintain sufficient attachment force between the lead and stimulator pod to remain operatively connected during a wide range of patient activities during which therapy may be needed. At the same time, the system may be able to disconnect the patient cable from the stimulator pod safely and/or comfortably without damaging and/or displacing the system and/or any of its components (e.g. lead, connectors, stimulator, pad, etc.) and/or without injuring or causing pain or discomfort to the patient. In other words, the system permits the connection between the patient cable and stimulator pod to remain mechanically and electrically connected when desired but also may enable safe disconnection when necessary (such as mechanically and/or electrically). This may also enable a patient to reconnect without clinician support (enables patient to safely resume therapy without having to return to clinician to have a lead, system, or other system component repaired, replaced, reprogrammed, and/or repositioned). In addition to protecting the lead connector (and the attached percutaneous lead) from accidental forces on the patient cable from catching or snagging on clothing, handled objects, or objects in the environment.

Specific embodiments of the present teachings may include any combination of the following features:
- a helical, wire electrode, carried within an introducer (e.g., a disposable hypodermic needle or sheath);
- an adhesive patch at least partially securing a proximal end of the electrode protruding from the body;
- a lead connector, fixed to the proximal end of the electrode;
- a patient cable detachably connected to the lead connector;
- a stimulator pod, including a power source and a return electrode, detachably connected to the patient cable and forming an electrical connection between the pod and the electrode to deliver therapeutic stimulation;
- a controller pod in communication with the stimulator pod;
- a programmer unit in communication in the controller pod and/or stimulator pod wherein the programmer unit selectively delivers instructions to inform the therapeutic stimulation;
- wherein the electrode, the lead connector, patient cable and stimulator pod form a series of detachable connections having tension and, in response to a disconnection force, at least one of the following occurs: the tension is temporarily reduced and the patient cable detaches from the lead connector;
- wherein at least one of the detachable connections is established by way of at least one selected from: a magnet and a releasable, spring-loaded connection, a connector having a predefined holding strength;
- wherein the programmer unit communicates with the controller pod by way of a wireless connection;
- wherein the needle includes at least one test stimulation electrodes, controlled by the controller pod to aid in the positioning of the electrode;
- wherein the needle includes at least one test stimulation electrodes, controlled by at least one of the controller pod and the programmer pod to aid in the positioning of the electrode;
- wherein the lead connector is bifurcated to enable connection of a plurality of electrodes;
- wherein the patient cable comprises a plurality of segments in which each segment is detachably connected;
- wherein a plurality of stimulator pods may be provided in combination with a plurality of electrodes and wherein the controller pod coordinates stimulation among the stimulator pods;
- wherein the stimulator pods communicate wirelessly with the controller pod;
- wherein the lead connection further comprises a mechanical connector that receives and holds the proximal end while maintaining an electrical connection between the electrode and the patient cable;
- wherein the mechanical connector releasably and resettably moves in response to the force;
- wherein the lead connector mechanically secures the lead and electrically connects to it in response to a force applied by the user;
- wherein the mechanical connector comprises a rotating element;
- wherein the mechanical connector comprises a funnel that may have a controllably collapsible segment and wherein the proximal end of the lead received through said funnel and said controllably collapsible segment engages a portion of the electrode close to the proximal end;

wherein the rotating element of the lead connector is electrically connected to the lead and to the series of detachable connections ending at the stimulator pod;

wherein at least one of the stimulator pod and the controller pod provide a user alert when a predetermined amount of force is applied, e.g., an amount to dislodge the patient cable;

wherein the user alert includes at least one of the following: a visual cue and an auditory cue;

wherein the magnet comprises at least one insert molded neodymium magnet;

wherein the magnet is shielded to reduce unintended magnetic fields and concentrate or focus the filed between the two ends of the breakaway mechanism;

wherein the tension is reduced to a predetermined level and, upon the force exceeding the predetermined level, the patient cable detaches;

wherein the predetermined level is less than or equal to a fraction (e.g., one half, 90%, 80%, 70% etc.) of a force required to change position of the lead connector on the body;

wherein at least one end of the patient cable includes a connection member that is mated to a corresponding connection member on at least one of the lead connector and the stimulator pod; and wherein there may be a plurality of mated connection members and each set of mated members has a unique shape to avoid improper connections.

A percutaneous electrical stimulator system may include an electrode percutaneously insertable into a patient, an adhesive bandage at least partially securing a proximal end of the electrode protruding from the patient, a lead connector, fixed to the proximal end of the electrode, a patient cable detachably connected to the lead connector, and a stimulator connected to the patient cable and forming an electrical connection between the stimulator and the electrode to deliver therapeutic stimulation.

The percutaneous electrical stimulator system describe above:

wherein the electrode, the lead connector and the patient cable form a series of detachable connections having tension and, in response to a disconnection force, at least one of the following occurs: the tension is temporarily reduced and the patient cable detaches.

wherein at least one of the detachable connections is established by way of at least one selected from: a magnet and a releasable, spring-loaded connection, a mechanical connection.

wherein a portion of the series of detachable connections is engaged via a rotating element, said rotating element adjusting the tension in response to the disconnection force.

further comprising a controller in communication with the stimulator.

wherein the stimulator communicates wirelessly with the controller.

further comprising a programmer unit in communication with the controller wherein the programmer unit selectively delivers instructions to inform the therapeutic stimulation.

wherein the programmer unit communicates with the controller by way of a wireless connection.

wherein at least one of the stimulator and the controller provide a user alert when the response to the force occurs.

wherein the user alert includes at least one of the following: a visual cue, tactile cue and an auditory cue.

further comprising a programmer unit in communication with the stimulator, wherein the programmer unit selectively delivers instructions to inform the therapeutic stimulation.

wherein the lead connector is plurally split to enable connection of a plurality of electrodes.

wherein the patient cable comprises a plurality of segments in which each segment is detachably connected.

wherein a plurality of stimulators are provided in combination with a plurality of electrodes and wherein the controller coordinates stimulation among the stimulator.

wherein the stimulators communicate wirelessly with the controller.

wherein the lead connection further comprises a mechanical connector that receives and holds the proximal end while maintaining an electrical connection between the electrode and the patient cable.

wherein the mechanical connector releasably and resettably moves in response to the disconnection force.

wherein the mechanical connector comprises a rotating element.

wherein the mechanical connector comprises a funnel with a controllably collapsible segment and wherein the proximal end received through said funnel and said controllably collapsible segment engages a portion of the electrode proximate to the proximal end.

wherein the magnet comprises at least one insert molded magnet formed from at least one of neodymium, samarium cobalt, alnico, and ferrite.

wherein the magnet is shielded to reduce unintended magnetic fields and/or to concentrate intended magnetic fields from the magnet.

wherein the tension is reduced to a predetermined level and, upon the disconnection force exceeding the predetermined level, the patient cable detaches.

wherein the predetermined level is less than or equal to a percentage of force required to change position of the electrode within the patient.

wherein at least one end of the patient cable includes a connection member that is mated to a corresponding connection member on at least one of the lead connector and the stimulator.

wherein there are a plurality of mated connection members and each set of mated members has a unique shape to avoid improper connections.

A percutaneous electrical stimulator system may include an electrode percutaneously insertable into a patient, a lead extending from the electrode, a lead connector, fixed to the lead, a patient cable detachably connected to the lead connector, and a stimulator connected to the patient cable and forming an electrical connection between the stimulator and the electrode to deliver therapeutic stimulation.

The percutaneous electrical stimulator system describe above:

wherein the lead is a helical wire lead with the electrode integrally formed at an end thereof.

A percutaneous electrical stimulator system may include a wire electrode percutaneously insertable into a patient, the electrode having a proximal end extending from the patient when inserted therein, a lead connector, fixed to the proximal end of the electrode, a patient cable detachably connected to the lead connector, a stimulator connected to the patient cable and forming an electrical connection between stimulator and the electrode to deliver therapeutic stimulation.

The percutaneous electrical stimulator system describe above:
further comprising a controller in communication with the stimulator wherein the electrode, lead connector and patient cable form a series of detachable connections having tension and, in response to a disconnection force, at least one of the following occurs: the tension is temporarily reduced and the patient cable detaches.
wherein at least one of the detachable connections is established by way of at least one selected from: a magnet and a releasable, spring-loaded connection.
wherein the electrode is covered by an electrical insulation except at a distal end thereof.
wherein the mechanical connector comprises a rotating element providing motion and force to cut or pierce the electrical insulation and to mechanically secure the lead.

These and other features and advantages of the present teachings are set forth in the following specification, drawings and claims.

BRIEF DESCRIPTION OF THE DRAWINGS

These and other features, aspects and advantages of the present disclosure are better understood when the following detailed description is read with reference to the accompanying drawings, in which.

DETAILED DESCRIPTION

Reference will now be made in detail to exemplary embodiments of the present teachings, examples of which are illustrated in the accompanying drawings. It is to be understood that other embodiments may be utilized and structural and functional changes may be made without departing from the respective scope of the present teachings. Moreover, features of the various embodiments may be combined or altered in any combination without departing from the scope of the present teachings. As such, the following description is presented by way of illustration only and should not limit in any way the various alternatives and modifications that may be made to the illustrated embodiments and still be within the spirit and scope of the present teachings.

As noted above, previous neurostimulation and neuromodulation systems have inherent weaknesses. For example, these weaknesses may include difficulty using the stimulator while it is mounted on difficult to reach position of the body, a position on the body that is subject to frequent movement, including, without limitation the patient's arm, back, leg, head, shoulder, etc. Further, it may be difficult for a clinician to couple the stimulator with the lead, including, without limitation a fine-wire lead and may be difficult for the clinician to work with the system while on the patient body. Further still another weaknesses may include inherent difficulty with operating the system while it is adhered to the body, a complex user interface, difficulty replacing bandages without fear of dislodging the electrode, and discomfort due to system size and shape. Certain embodiments of the present teachings overcome these weaknesses and provide additional advantages, as will be recognized by persons of skill in this field.

Figure 1:
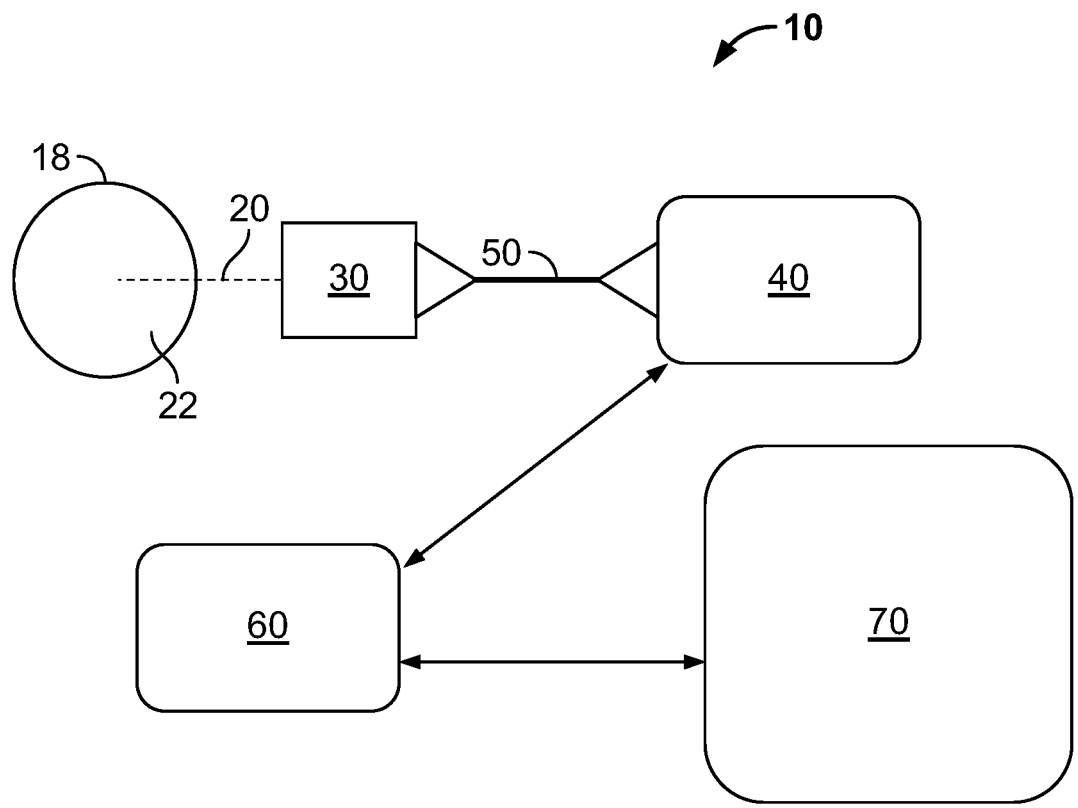
FIG. 1 is a schematic representation of one embodiment of the present teachings.

FIG. 1 schematically illustrates components of one embodiment of the invention. The percutaneous stimulation system 10 may include an electrode, such as a fine-wire electrode 18. The electrode 18 may be initially introduced to the body by way of a hypodermic needle (not shown) or any other method of insertion. The present teachings are not limited to a specified type of insertion method or apparatus. Any appropriate system may be utilized without departing from the present teachings. The electrode 18 may include a lead 20 extending therefrom such as a micro-lead, fine-wire lead or simply lead. The lead 20 may possess a generally small diameter in comparison to previous systems, with optimal sizes of less than 1.0 mm and, more preferably, less than 0.6 mm. Further, the electrode 18 and/or lead 20 may have a generally coiled or helical structure, rather than a smooth cylinder. However, the present teachings are not limited to this structure. Any appropriate configuration may be utilized without departing from the present teachings.

For the sake of clarity, the term "proximal" in the context of this application typically refers to the end of the electrode that is not inserted into the body and "distal" typically refers to the electrode end that is inserted into the body near the nerves. Depending upon the manufacture of the electrode structure, this proximal end may be wrapped in an insulating or protective coating or wrap. To the extent electrical connections must be made with the proximal end, the components at issue will allow for the removal of such coating(s)/wrap(s).

After the electrode 18 is positioned within the body 12 at a desired therapeutic location, the proximal end of the electrode may be covered by an adhesive bandage 22 and attached to a lead connector 30. The adhesive bandage 22 may have an adhesive to at least partially cover and, in some instances, guide the proximal end toward the lead connector 30. The adhesive bandage 22 may take any number of shapes, including, without limitation the shape depicted in FIG. 2A, and the adhesive may be selectively applied to portions of the periphery to better ensure that the proximal end is not inadvertently ensnared when making the necessary connections within the system 10. The adhesive bandage 22 may be made of any appropriate thin film material, such as polyethylene, and with one or more optional absorbent pads and/or non-adhesive removal tabs. The adhesive bandage 22 may also be carried on a disposable backing that may release the adhesive bandage 22 immediately prior to its application on the body 12.

Embodiments of the adhesive bandage 22 are shown in FIGS. 6-11. The adhesive bandage 22 may eliminate the need for a separate tape to secure the lead connector 30. The adhesive bandage 22 may be an integral system component that may generally protect the lead 20 exit site by managing exposure to potential contaminants (e.g., water, dirt, pathogens, virus, bacteria, etc.), thus helping to prevent infection of the site. The adhesive bandage 22 may further generally protect the lead 20 and more specifically the electrode 18 from accidental dislodgement caused by snagging (e.g., on a body part, clothing or furnishings). The adhesive bandage 22 may also generally secure the lead connector 30 to the patient's skin to isolate the lead 20 from forces applied to the lead connector 30, such as during system 10 maintenance and daily activities of living. The adhesive bandage 22 may be a covering bandage that integrates with the lead connector 30 to allow the user to easily and consistently remove and replace the adhesive bandage 22 without fear of inadvertently pulling the lead 20 and/or electrode 18. The adhesive bandage 22 may include a film body 42 and skin adhesive 44 that ensures that adhesion to skin will be appropriate for use on human skin. The film body 42 may be of any appropriate material, including, without limitation a clear polyethylene or any other material that generally protects a wound and discourages infection. The adhesive bandage 22 may be of any appropriate shape, including, without limitation a generally elliptical shape. The skin adhesive 44 may be applied along the perimeter such that the lead 20 is not exposed to any skin adhesive 44. The skin adhesive may 44 may have the appropriate amount of tackiness to generally prevent inadvertent release from the skin. The skin adhesive 44 may extend generally around the perimeter of the film body 42 of the adhesive bandage 22. This may create a seal to generally prevent contaminants from entering anywhere around the entire perimeter. Further, this may make the adhesive bandage 22 easier to remove so that it does not stick to the lead 20 upon removal.

The adhesive bandage 22 may include a cutout section 48 over the lead connector 30 that may eliminate gaps in the seal and allows the user to use a finger to hold the lead connector 30 firmly against the skin during replacement of the adhesive bandage 22. As noted above, the lead connector 30 and adhesive bandage 22 may be contoured to fit together—this may result in a better seal. The adhesive bandage 22 may include a removal tab 56. A patient and/or clinician can put his or her finger over the bandage portion 52 and lead connector 30 to generally prevent the lead 20 and electrode 18 from pulling from the skin. This may be particularly useful in difficult to reach positions on the patients body and on body parts with frequent movement, e.g., legs, arms, back, head, etc.

The film body 42 of the adhesive bandage 22 may include a generally see-through, translucent, clear, etc. body with a bandage portion 52. The bandage portion 52 may include an absorbent pad configured to generally absorb any fluid exiting the lead insertion site, e.g., any kind of liquid (including, without limitation, blood) that may ooze from the lead insertion site will be absorbed into the bandage portion 52. The size of the bandage portion 52 may still allow the patient and/or clinician to view the area around the lead exit site to determine the existence of any infections. Having the clear film body 42 further allows the patient and/or clinician to view the lead exit site. The adhesive bandage 22 may help keep fluid from obstructing a view of the skin to help identify if any infections are present on the patient.

Figure 3A:
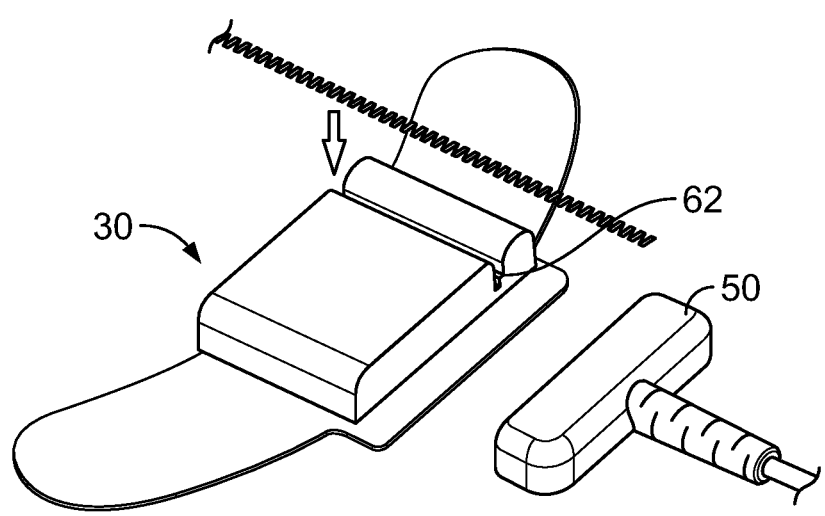
FIGS. 3A, 3B and 3C are diagrammatic representations of the lead connector used in various embodiments of the present teachings.
Figure 3B:
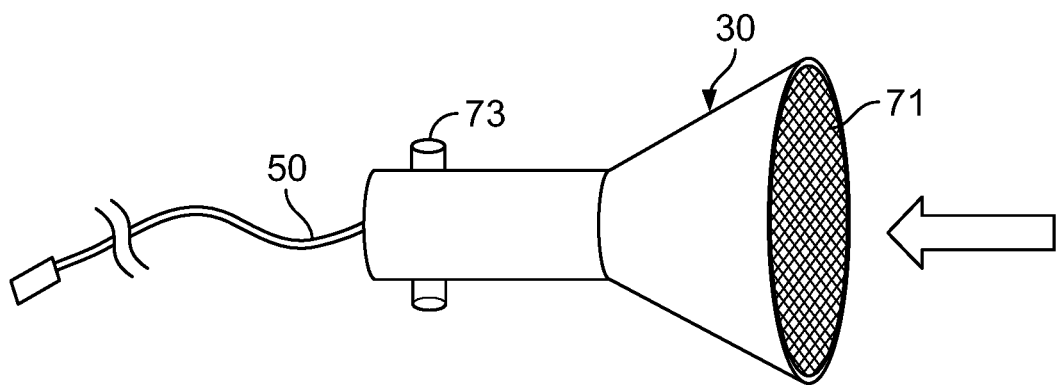

Further, the proximal end of the electrode 18 or lead 20 may be received by and coupled to the lead connector 30. The lead 20 is fed into the lead connector 30 via a slot 62, funnel 71 or other guide, as generally depicted by the arrows in FIGS. 3A and 3B. Once the lead 20 is received, coupling may occur compressively by collapsing a portion of the structure, using a screw, a sliding plate, a lever, friction fit, bayonet, magnet, gripping tabs or other physical means that allow a user to couple the pieces with only one hand. Upon collapse or compression, the lead connector 30 may be fixed to the proximal end of the electrode 18 or lead 20. In some embodiments, the lead connector 30 may include gripping teeth, blades or other implements that enhance an interference or friction to securely grip the lead 20. In some cases, the element connecting the lead connector 30 to the electrode 18 may also serve to remove unwanted insulation or coatings from the surface of the proximal end of the electrode 18, thereby improving both the mechanical and electrical contact established by lead connector 30. The lead connector 30 may fix the lead 20 in a manner that involves only one hand, by either the clinician or the user.

The present teachings may include designs to facilitate the use of the lead 20 and electrode 18 for testing, a non-limiting example being the lead connector 30 that may electrically and operatively connect the proximal end of the lead 20 to an external stimulator pod 40 via a wire, such as a patient cable 50, quickly and effectively. The patient cable 50 may be of any appropriate configuration and may provide a strong/stable mechanical and/or electrical connection. This configuration may reduce the duration of the procedure to install on the patient. Being able to easily remove the lead connector 30 also may reduce the procedure time. A non-limiting example may include a lead connector 30 having a funnel end 71 such that an end of the lead 20 can easily be inserted into the funnel 71. The funnel 71 may guide the lead 20 into the lead connector area, where teeth, loops, or surfaces that are spring-loaded may be manipulated by the user via levers or buttons to clamp onto and create an electrical connection with the lead 20. This lead connector 30 may have a wire and plug attached with allows for connection with an external stimulator. The funnel 71 may make it easier to guide a small lead therein. The funnel 71 may guide the proximal end of the lead towards an area where mechanical and electrical connection with the electrode may be formed, for example by an internal clip actuated by an external control (e.g., a button, lever, or other means of controlling a connection).

Figure 3C:
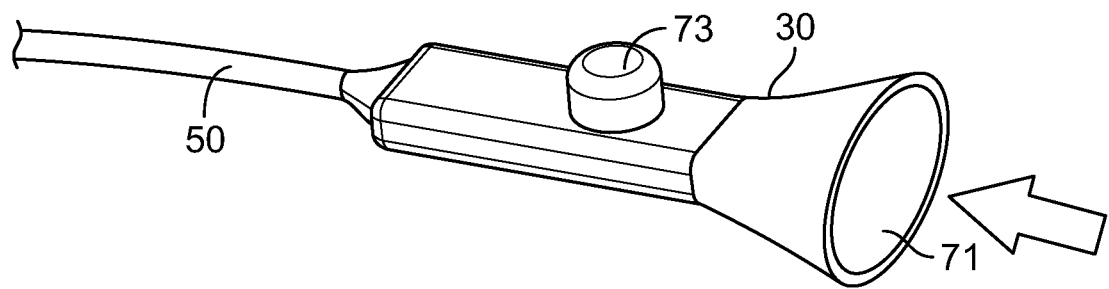

An exemplary embodiment of the lead connector with a funnel end 71 is shown in FIG. 3C. The funnel 71 may ease insertion of the proximal end of the lead (arrow pointing where lead end would be inserted). The lead connector 30 may include a button 73 located on a top portion of the lead connector 30, which is a non-limiting example of a mechanism by which the actual connection to the lead (internal, not shown) may be made/controlled. The patient cable 50 may be attached to the lead connector 50 in any appropriate manner and may allow for easy connection to the other components such as the simulator pod 40.

The lead connector 30 may eliminate the need for a separate tool. It may allow a one-handed mechanism for the clinician and/or patient, including, without limitation it may include a push mechanism. The lead connector 30 may be of any appropriate configuration. By way of a non-limiting example, the lead connector 30 may include plastic unit (e.g., manufactured by insert molding) with an insulation displacement connector (IDC) mechanism that strips the insulation from the lead 20 in order to make electrical contact. The lead 20 may be placed in a slot 62 with a contact strip with micro-structured barbs that hold the lead 20 in place until the IDC mechanism is implemented with a one-handed push mechanism. The lead connector 30 may also be employed for each detachment from (e.g., magnet, spring or other mechanism) and re-attachment.

On the side of the lead connector 30 a breakaway mechanism 54 may be utilized. The breakaway mechanism 54 may include a connector that allows for quick detachment and easy re-attachment (e.g., magnet or spring-loaded mechanism). However, the present teachings are not limited to this configuration. The breakaway mechanism 54 may be operatively attached with the patient cable 50, i.e., the portion of the lead 20 between the lead insertion site and the stimulator pod 40. This may enable mechanical and/or electrical connection between the lead 20 and patient cable 50 and/or stimulator pod 40. The breakaway mechanism 54 may be of any appropriate configuration that applies a predetermined force between a connection point or connection points between the lead connector 30 and patient cable 50, between portions of the patient cables 50 and/or between the patient cable 50 and stimulator pod 40. The breakaway mechanism 54 may be configured such that when a predetermined force is applied to the patient cable 50 it becomes dislodged from either of the lead connector 30, another portion of the patient cable 50 and/or the stimulator pod 40. The breakaway mechanism 54 may comprise a mechanical connection, electrical connection, a magnetic connection or any combination of such (a detachable and re-attachable connection), including, without limitation a hook and loop system similar to Velcro. These may operatively interact to provide a predetermined holding force so that when an amount of force exceeding this predetermined holding force the breakaway connector 54 releases. The present teachings are not limited to a specific configuration.

The breakaway mechanism 54 may use insert molded Neodymium magnets by way of a non-limiting example. In other embodiments, a different permanent magnet may be utilized, such as a Samarium Cobalt, Alnico, Ceramic, Ferrite, or other rare earth magnets. In addition or in the alternative, a spring-loaded (or any biasing member) conductive pin (including, without limitation a gold, gold plated, metallic, or any other conductive material pin) connector may be located on the patient cable 50 and a mating conductive element configured to operatively engage with the conductive pin may be located on the lead connector 30 body. The conductive pin may be formed of any conductive material, including, without limitation being a generally flat gold plated contact. The conductive pin may be of any configuration and may adjust position relative to the mating conductive element.

This may provide the predetermined holding force noted above. The present teachings, however, are not limited to this configuration. Any configuration of biasing member may be utilized to apply a predetermined force between the lead connector 30 and patient cable 50 (or in the alternative or in addition between portions of the patient cable 50 and/or between the patient cable 50 and stimulator pod 40).

The lead connector 30 may eliminate the need for a separate tool—it may utilize a one-handed push mechanism. Further still, the lead connector 30 may include the breakaway mechanism 54 of any appropriate embodiment between the patient cable 50 and/or between the patient cable 50 and the stimulator pod 54. Further still, any number of breakaway mechanism 54 may be utilized, e.g., one, two, three, etc. Each such breakaway mechanism 54 may be positioned on a different portion of the system, e.g., on the lead connector 30, on the patient cable 50 (any number may be utilized) and/or on the stimulator pod 40. Multiple breakaway mechanism 54 may be utilized to ensure that the break away occurs regardless of where the force is applied.

The lead connector 30 may be configured to enable the adhesive bandage 22 to remain secure during use (e.g. locking out water and/or contaminants) while also enabling safe and easy removal. The lead connector 30 and adhesive bandage 22 may configured to allow change, application, and/or re-application of the adhesive bandage 22 while minimizing risk of displacing or dislodging the lead 20, lead connector 30, and/or any other system components. The lead connector 30 may mate with the adhesive bandage 22 to eliminate the need for multiple tapes and minimize the fear of lead dislodgement while performing bandage replacement. Further, the overall system may have a lower profile, including, by way of a non-limiting example having a 30% lower profile. For example, the lead connector 30 may have a low profile that may help reduce the likelihood of a patient "snagging" or inadvertently catching the lead connector 30 on an item. Having the low profile may reduce the chance of this occurring. The lead connector 30 may have a profile that when attached with the patient may extend from the patient slightly more, even with, or slightly below the adhesive bandage 22.

Additionally or alternatively, the connector 30 may have a rotating element, such as a knob, dial, spool or post. The rotating element may engage the lead 20, mechanically and/or electrically, in order to assist in adjusting the tension of the detachable connection (e.g., the breakaway mechanism 54) having tension formed by the electrode 18, the lead connector 30 and the patient cable 50. The rotating element may include a predetermined tension release or recoil mechanism that responds to a disconnection force by releasing excess lead that is wound around the element. In the same manner, the lead connector 30 may accomplish this tension release by slider or other movement that need not be rotational in nature. As with the detachable aspects of the patient cable 50 connections, the tension release may occur at a force that is less than or equal to one-half the force required to dislodge or move the electrode 18 from its initial position.

The lead connector 30 may be bifurcated or split into multiple divisions to receive a plurality of electrodes 20. For example, multiple slots or funnels can connect multiple electrodes to a single stimulator pod 40 (or a plurality of stimulator pods 40) to enable therapeutic stimulation to be provided to separate parts of the body.

Figure 4A:
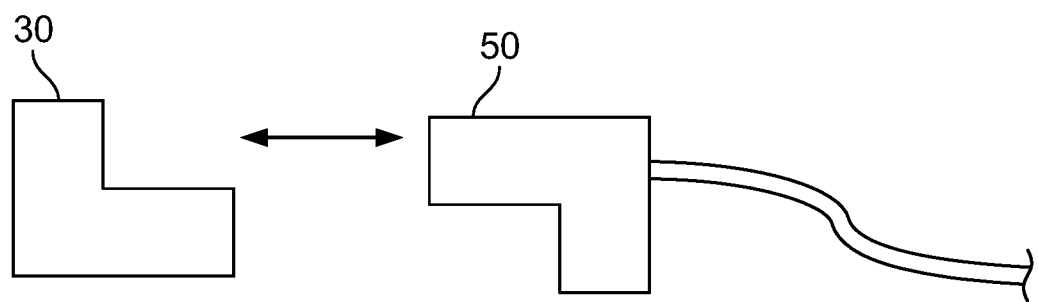
FIGS. 4A and 4B diagrammatically illustrate potential mating connections for the magnets and other detachable connections.
Figure 4B:
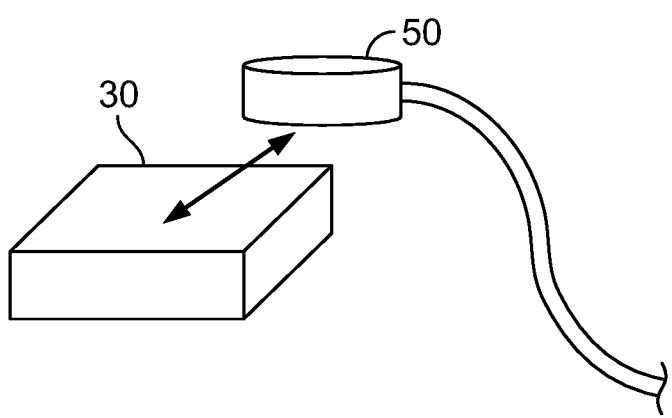
Figure 5:
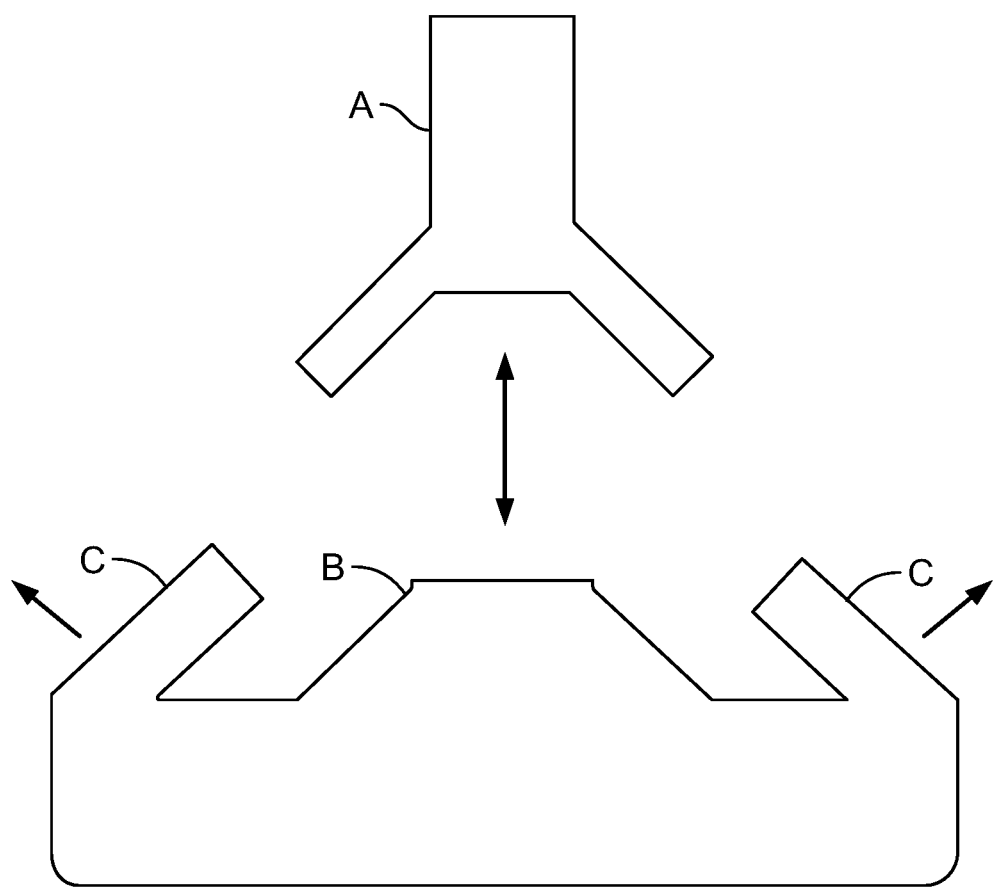
FIG. 5 diagrammatically illustrates a spring-loaded and/or magnetic connection that can be used in the detachable connections.

In other embodiments, the connection between the lead connector 30 and patient cable 50 may be detachable—this detachability may be of any appropriate configuration, including, without limitation the break away mechanism 54. The detachability may include, without limitation, magnets, such as insert molded neodymium magnets, that may be formed on the lead connector 50 and one or both ends of the patient cable 50 (if on both ends, the stimulator pod 40 would also have a detachable connection as described herein). Depending on the manufacturing process, the magnets, and how the magnets are fitted together, may allow for differentiating the points of connections. For example, the lead connector 30 may have a stepped connection port that fits with a correspondingly stepped connection on one of the patient cable, as illustrated in FIG. 4A. Alternatively, a circular magnet may sit on the top of the connector lead, also shown in FIG. 4B. A slight indentation or groove or other releasable force fitting could be provided to allow for the experience of a "snap-in" feel. In other embodiments, any mating shapes may be utilized such that the patient or clinician may insert one portion into another or otherwise engage the two components together—see for example FIG. 5. Further, the present teachings are not limited to the shape and size of magnets shown and disclosed. Any appropriate shape or sized magnet may be utilized in these embodiments. The shape and size of the magnets may be the same, mating shape, or different shapes. Further, the breakaway mechanism 54 may not utilize magnets but may include mechanical connections of any type, shape and/or size that release from one another upon application of a specific amount of force. Regardless of configuration, the breakaway mechanism 54 may reduce the risk that force on the patient cable 50 is transferred to the lead 20 or more specifically to the electrode 18 inserted into the patient. The configuration may allow for easy attaching and easy re-attachment.

In addition to or in place of magnets, a biasing fitting may be utilized—such as a spring-loaded member. The fitting is described generically so that it may be employed on any of the components, although particular utility is expected at the connection between the lead connector 30 and the patient cable 50. End A has an inverted Y shape that mates with a corresponding shaped end B. Additional shapes, prongs or members may be included. The outermost arms C move, such as in a spring-loaded or magnetic fashion, to receive and release end A (single ended arrows indicate a preferred range of motion). Ends A and B may be fitted in the plane parallel to the double arrow and/or they may be dropped or snapped into place and then released in a direction that is different than, preferably including perpendicular to, the direction of release.

In some embodiments, the break away mechanism 54 may be configured such that neither the stimulator pod 40 not the lead 20 (or more specifically the electrode 18) are displaced if unwanted force is applied to them or their connection(s). For example, the connection between the patient cable 50 and the stimulator pod 40 may be detachable upon application of a predetermined force. The predetermined force may be calculated to generally prevent movement of the electrode 18 once placed in the appropriate position within the patient.

Alternatively, or in addition, the patient cable 50 may itself be detachable (e.g. in the middle so that it actually is a plurality of patient cables, e.g., 2 or more). The patient cable 50 may be detachable at any point between the lead 20 and the stimulator pod 40, e.g., patient cable 50 may disconnect at either end. Further still, the predetermined detachable portion may be between the patient cable 50 and stimulator pod 40, along any portion of the length of the patient cable 50. For example, two or more patient cables 50 may be selectively attached at a detachment point to disconnect upon application of the predetermined force. Further, while the present disclosure notes that the portions are detachable, they may also be attachable. This may allow the system to serve as a failsafe mechanism to prevent damage and/or injury to the system, components, and/or the patient. The detachable portion may comprise the breakaway mechanism 54 described above or any other kind of appropriate detachable member.

In addition to just safely detaching, the circuitry in any of the patient cable 50, lead connector 30, and/or stimulator pod 40 may prevent delivery of unwanted stimulation in the event of a disconnection during stimulation, such as when multiple leads and/or patient cables may be utilized. By way of a non-limiting example, the patient cable 50 may be a "smart cable" that has components in addition to a path for electrical conduction that minimizes the risk of the patient experiencing unwanted stimulation (e.g., minimizes or eliminates the potential for the patient to experience a shock) when the patient cable 50 is disconnected unexpectedly during use. For example, the patient cable 50 may, when disconnected from either of the lead connector 30 and/or the stimulator pod 40 prevent further stimulation.

All of the above-mentioned connections rely on mated parts. In order to avoid improper installation, each of the mated pairs could be given a unique shape. Sensors or other circuitry may be employed at the connections points to better enhance the user alert feature described herein. Such sensors or circuitry could be inherent to the electrical signal delivering the stimulation, or separate signals could be established.

The patient cable 50 may mechanically and/or electrically connect the lead connector 30 and controller pod 40. Any durable, flexible material may be used for the patient cable 50. Patient cable 50 may also deliver power to and/or from the connected elements, or independent power supplies may be provided. The power supply for the system 10, and particular the stimulator pod 40 and controller pod 60 may be disposable or rechargeable, and any number of batteries or other power devices (e.g., capacitors, fuel cells, etc.) may be incorporated, depending upon the form factor and power requirements of the system.

In the event a plurality of patient cables 50 is used to establish a connection between the electrode/lead connector 30 and the stimulator pod 40, each segment of the patient cable 50 may rely on the quick release connections described above. In this manner, the risk of unintended force (e.g., snagging on clothing) repositioning or dislodging the electrode 18 is further minimized, particularly if the stimulator pod 40 cannot be placed proximate to the lead connector 30. Utilizing a plurality of segments in the patient cable 50 also improves the overall adaptability of the system.

The housing and/or materials selected for the lead connector 30 should be consistent with its design and purpose. At least portions of the lead connector 30 will be constructed from sufficiently conductive material to carry electrical pulses and signals from the stimulator pod 40 (such as via patient cable 50). Magnetic shielding may be selectively employed to minimize the creation of unwanted magnetic fields.

Figure 2A:
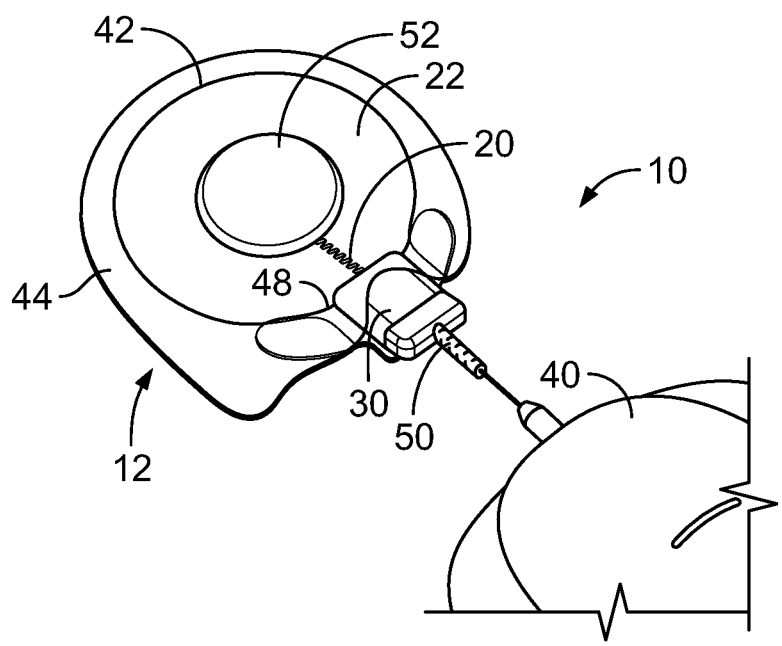
FIGS. 2A and 2B illustrate selected components in one embodiment of the present teachings.
Figure 2B:
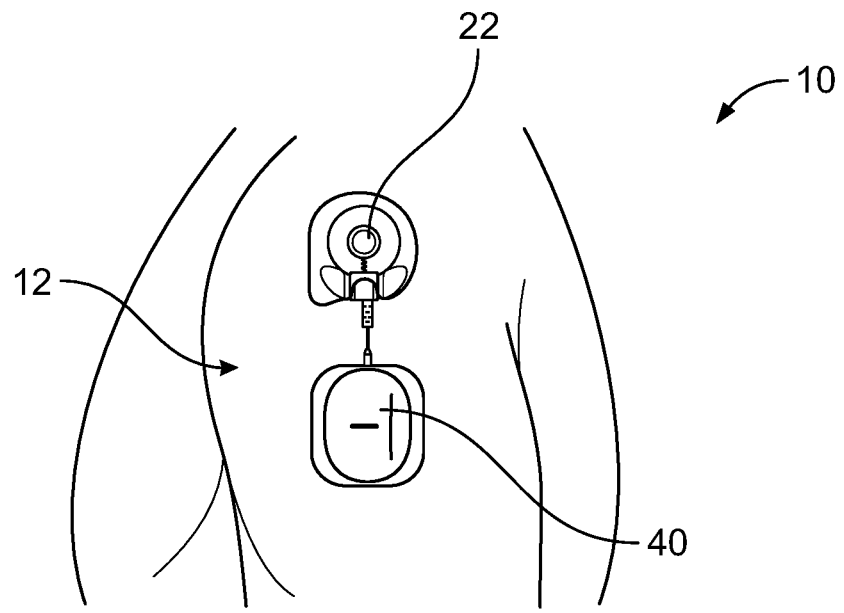
Figure 6:
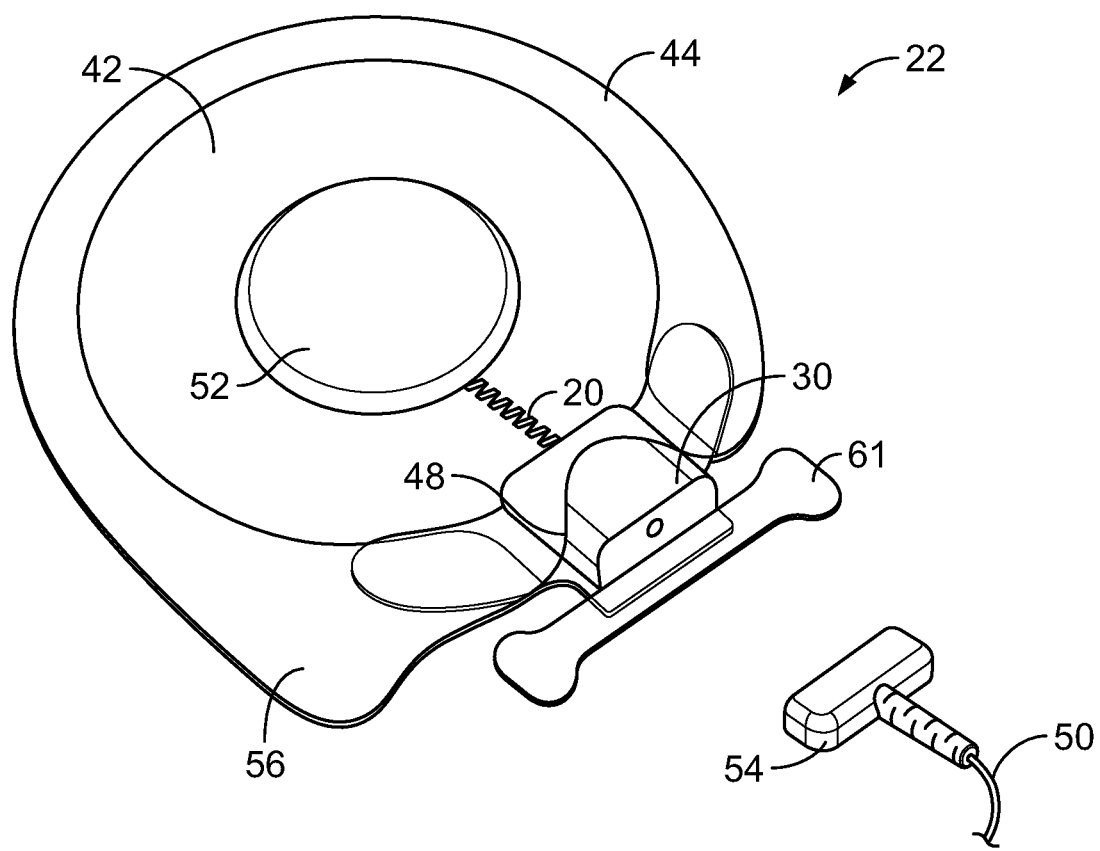
FIG. 6 is a perspective view of an embodiment of an adhesive bandage of the present teachings.
Figure 7:
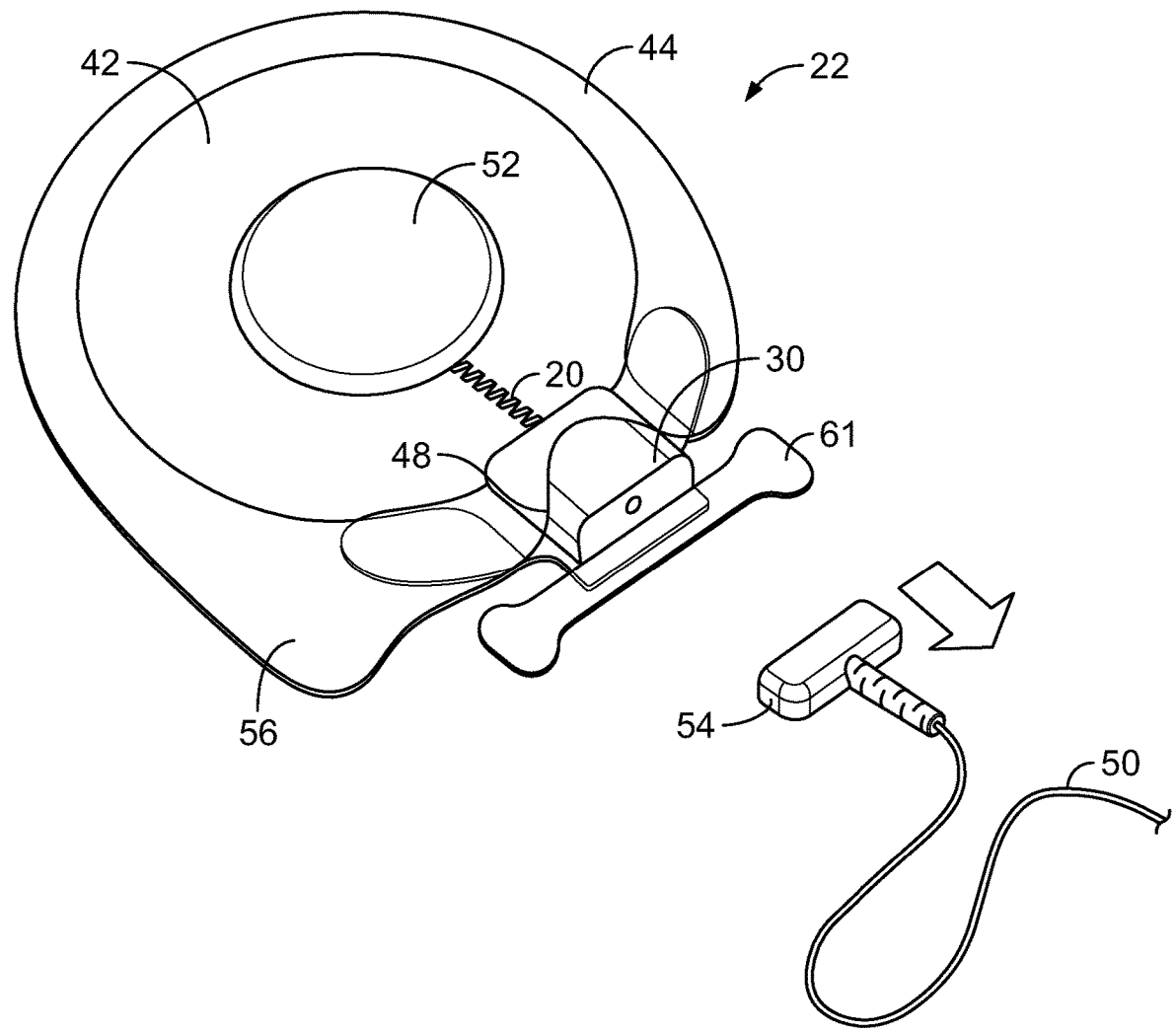
FIG. 7 is a perspective view of an embodiment of an adhesive bandage of the present teachings attached to a patient.
Figure 8:
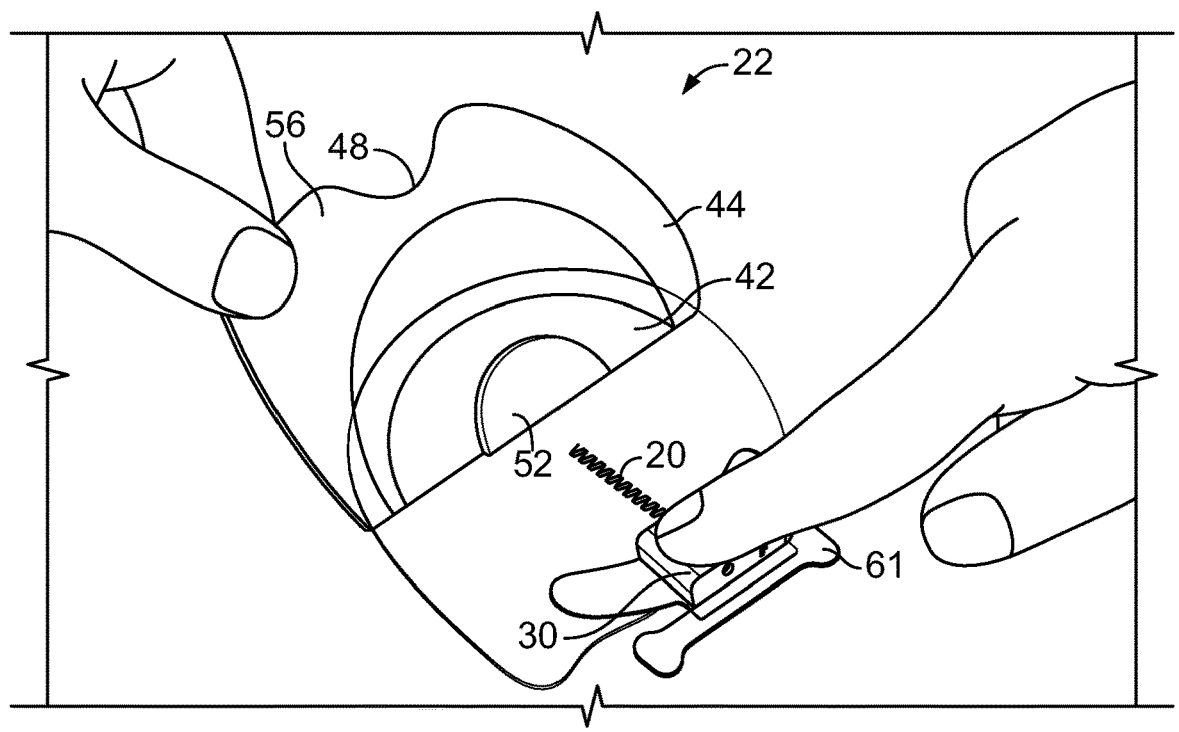
FIG. 8 is a perspective view of the adhesive bandage being removed from the patient.
Figure 9:
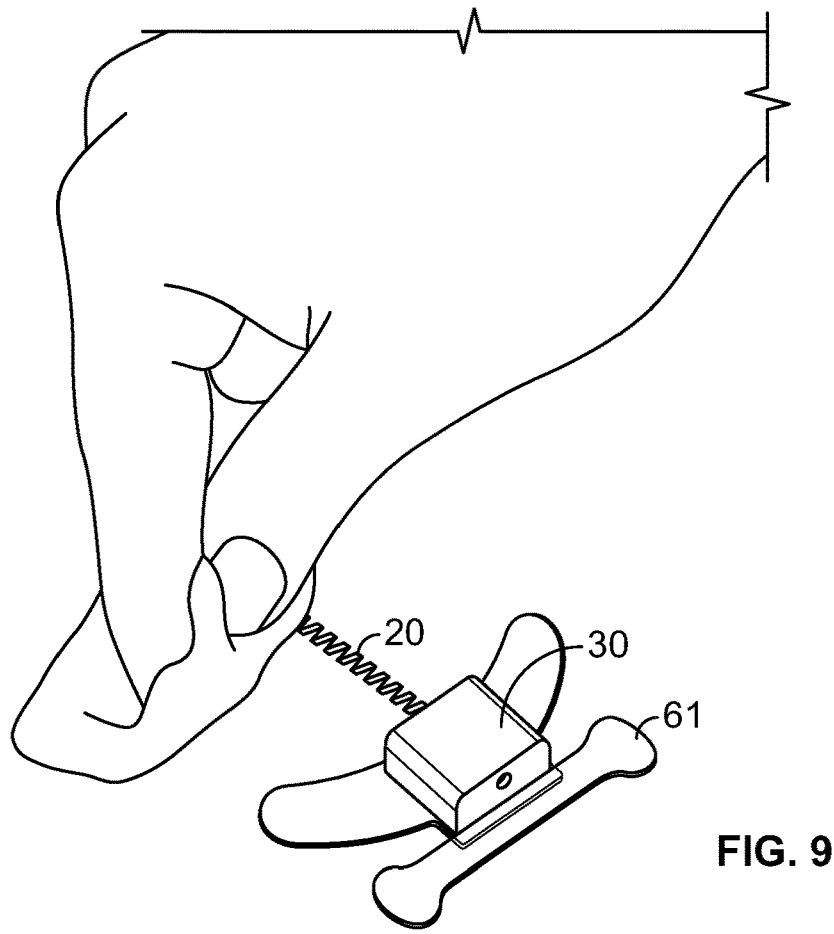
FIG. 9 is a perspective view of the patient with a lead inserted at an insertion site with the lead connector attached to the lead and adhesive bandage removed.
Figure 10:
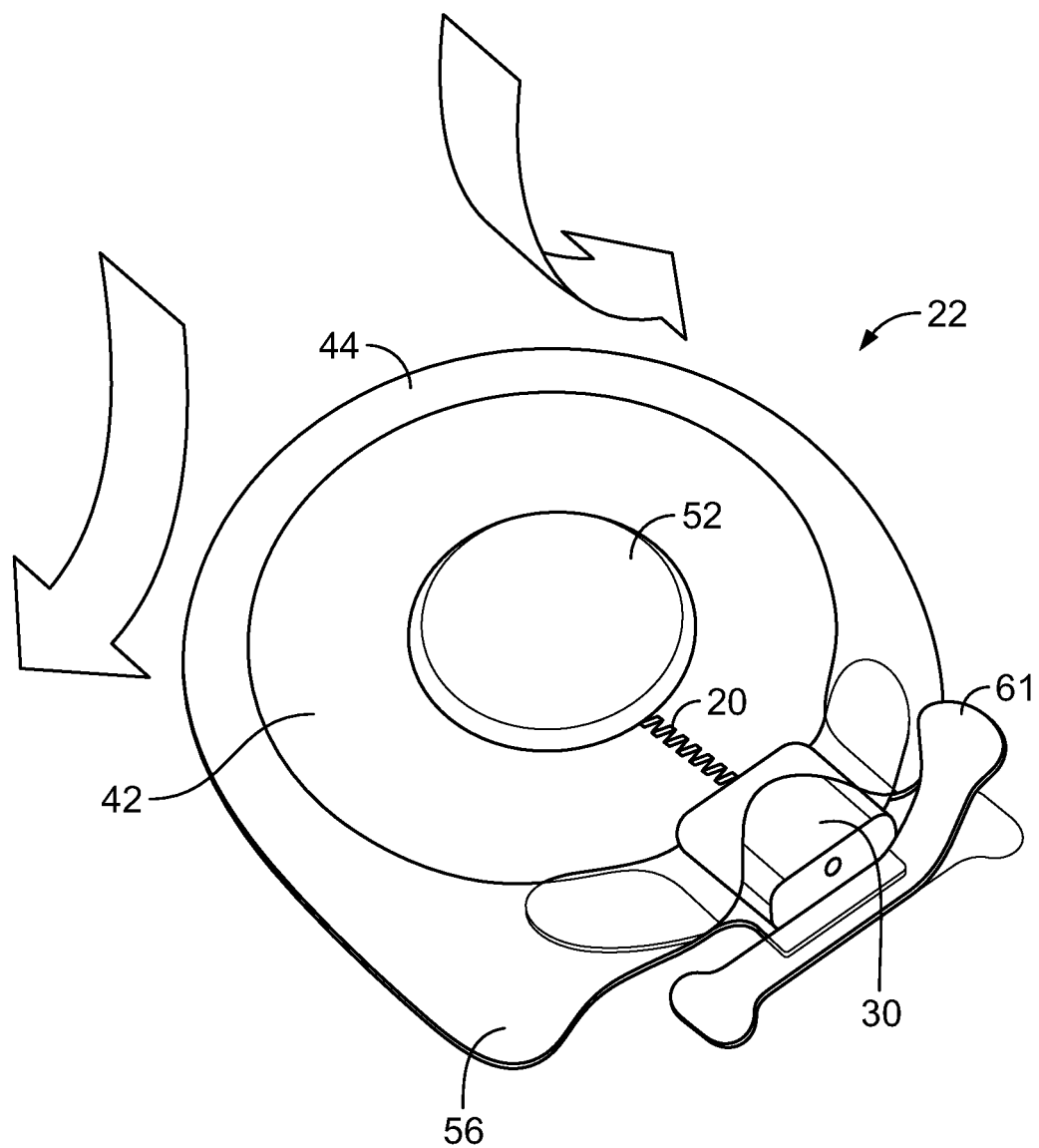
FIG. 10 is a perspective view of the adhesive bandage being attached to a patient.
Figure 11:
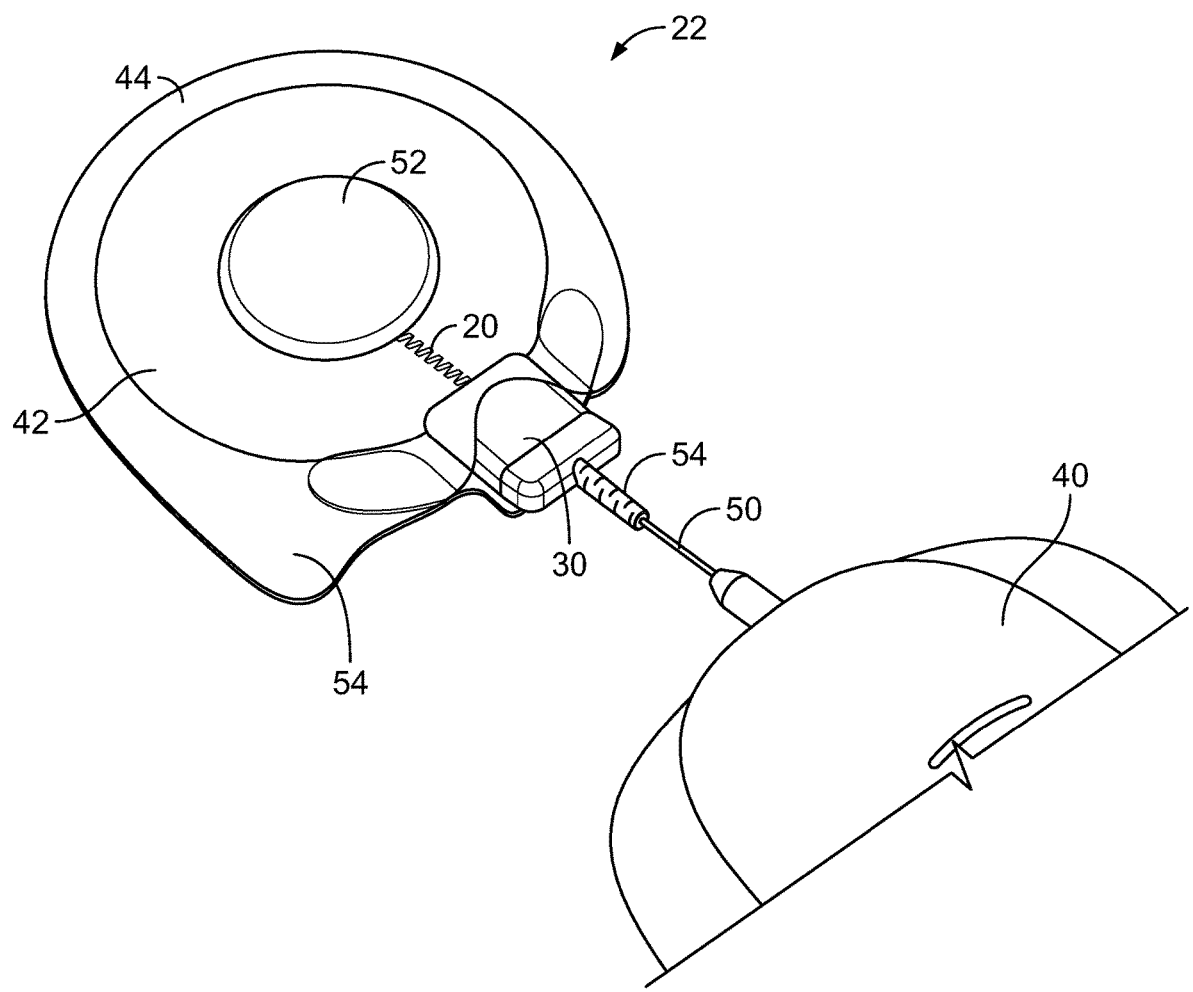
FIG. 11 is a perspective view of the lead connector operatively attached with the stimulator pod through the patient cable with the adhesive bandage attached to the patient.

In an embodiment depicted in FIG. 2A, the lead connector 30 may be attached to the body 12. This attachment may be made by way of adhesives, straps or other means. In one embodiment, at least a portion of the lead connector 30 is engaged by the adhesive bandage 22. The lead connector 30 may be sufficiently lightweight and/or located in sufficient proximity to other system components that are affixed to the body 12, so that the lead connector 30 may simply move freely as part of the detachable connection having tension formed by the electrode 18, the lead connector 30 and the patient cable 50. As shown in FIG. 6, a temporary tape strip 61 may be utilized to hold the lead connector 30 in place so as to operatively attach the break away mechanism 54. The temporary tape strip 61 may not be utilized in some embodiments.

The stimulator pod 40 may contain a programmable memory unit and circuitry necessary to deliver the therapeutic stimulation inherent to system 10. Further, the stimulator pod 40 may be designed to eliminate the need for a separate return electrode. The stimulator pod 40 may also contain a graphical user interface to communicate with the user. The stimulator pod 40 may include an LED or other visual indicia to communicate actions, errors or other pertinent information about the operation of the system. The stimulator pod 40 may also allow for user and/or clinician adjustments to the operation of the system. Further still, the stimulator pod 40 may communicate with a controller unit, either via a physical or wireless connection. Cables, wires, Bluetooth and other wireless technologies are all expressly contemplated. In some embodiments, the controller pod 60 may either have or not have a user interface integrated with it and/or remote (e.g. wireless such as Bluetooth). The present teachings are not limited to any such configuration.

The controller pod 60 may provide a more extensive graphical user interface, and it may be the primary means of initiating and altering the therapy, however, the present teachings are not limited to such. As with the stimulator pod 40, controller pod 60 may communicate via physical wires/cables or wirelessly with the stimulator pod 40 (or pods, if multiple pods are included in the system) and the optional programmer unit 70, described below. The controller pod 60 may be relatively larger than the stimulator pod 40, although wireless connectivity may allow the user to carry the controller pod 60 in clothing and/or generally at a convenient distance and location in comparison to the electrode 18 and stimulator pod 40.

While the stimulator pod 40 and controller pod 60 may both have a low profile and lightweight features, the programmer unit 70 may be a fully capable computer that can transmit detailed therapeutic instructions/regimens, error logs, usage logs and/or other information generated by the system 10. In some embodiments, the programmer unit 70 may remain in possession of the clinician, insofar as it enables a wider range of therapies, and the mobile and portable aspects of the other components in system 10 are inherent only to the user. The programmer unit 70 may communicate with the stimulator pod 40 directly or indirectly via the controller pod 60.

By way of example rather than limitation, the system 10 is expected to have particular utility in the treatment of post-stroke shoulder pain by way of percutaneous stimulation via a fine-wire lead in the deltoid muscle to stimulate branches of the axillary nerve. The therapy is delivered for a period of time, after which the lead is removed using gentle traction. The duration of daily therapy may range between 1 and 12 hours, with 6 hours as a preferred duration. The daily therapy may be administered over a period of days, weeks or even months, with 30 days anticipated to have the most benefit. The stimulation pulses and parameters may be varied, but the preferred range is less than 25 Hz, with some therapies particularly effective in the range bounded by separate lower and upper limits selected from: 1, 5, 10, 12, 15, 18 and 20, although other limits are contemplated. The amplitude is preferably centered at 20 mA, although any value between up to 50 mA or more may be useful. The pulse durations last anywhere from 5 microseconds to 200 microseconds or more, with minimal average pulse duration of 32 μs (range: 5 μs-75 μs); optimal average pulse duration of 70 μs (range: 10 μs-150 μs); and maximum tolerable average pulse duration of 114 μs (range: 25 μs-200 μs). Notably, tests have shown that electrical stimulation according to the system 10 for this purpose has both short term and long-term benefits that are not fully realized by the alternative treatment methods noted above.

While post stroke shoulder pain application is described above, the present teachings are not limited to any specific treatment or indication. It may apply to any kind of treatment, including, without limitation post-surgical pain patients or any type of pain patients, especially chronic pain patients (e.g. neuropathic pain, headache, and/or back pain patients).

Additional embodiments of a percutaneous stimulation system according the present teachings are described below. In the descriptions, all of the details and components may not be fully described or shown. Rather, the main features or components are described and, in some instances, differences with the above-described embodiment may be pointed out. Moreover, it should be appreciated that these additional embodiments may include elements or components utilized in the above-described embodiment although not shown or described. Thus, the descriptions of these additional embodiments are merely exemplary and not all-inclusive nor exclusive. Moreover, it should be appreciated that the features, components, elements and functionalities of the various embodiments may be combined or altered to achieve a desired percutaneous stimulation system without departing from the spirit and scope of the present invention.

Figure 12:
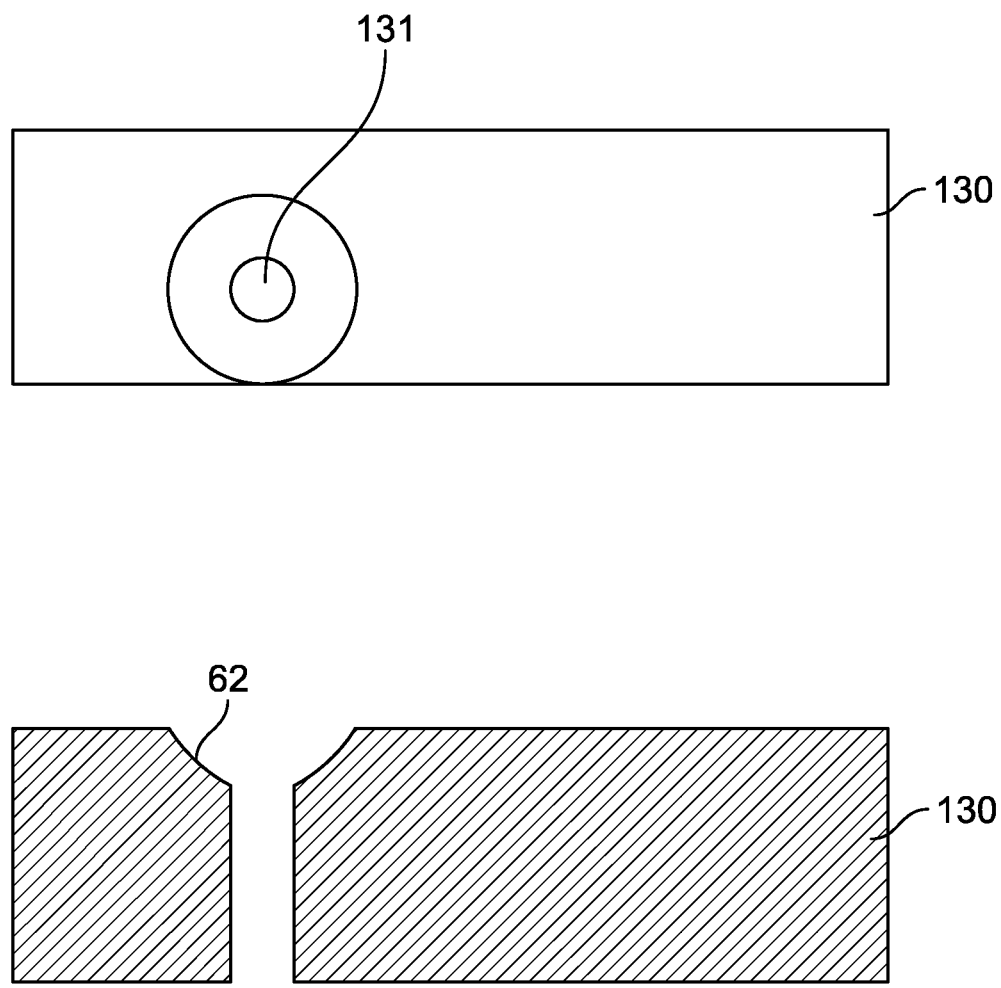
FIG. 12 are schematic views of embodiments of a lead connector.

A lead connector 130 may be designed to couple to the percutaneous lead easily. In a non-limiting example, the lead may be inserted through an aperture 131 in the lead connector, and the lead may go through partially or completely through the aperture 131. The aperture 131 may include a funnel shape where the lead is inserted to enable easy insertion into the aperture—See FIG. 12. In another non-limiting example, the lead may be placed into a slot or channel in the lead connector 130. In another non-limiting example, the lead connector may be composed of two or more components with the lead placed between and/or within the components, and the components may be secured together (e.g., slid together, snapped in place, twisted/ screwed onto one another, etc.) to couple to the lead. In some embodiments, the lead connector 130 may enable easy one-handed insertion and coupling of the lead to the system while remaining mechanically and electrically secure and prevents the patient from decoupling the lead (or electrode) intentionally or unintentionally.

The lead may be coupled to the lead connector electrically and mechanically. The mechanism by which the lead may be coupled mechanically to the lead connector 130 may be separate or the same as the mechanism by which the lead is coupled electrically to the lead connector 130. The user may couple the lead to the lead connector 130 using a component including, but not limited to, a knob, button, switch, or dial.

The lead connector 130 may be decoupled from the lead, and may allow the lead to be reconnected to the lead connector 130 at a different point along the lead (e.g., closer to or farther away from the stimulating portion of the lead or electrode). In a non-limiting example, the lead connector 130 may include a lock to prevent the patient from disconnecting the lead. The lock may be opened using, for example (but not limited to), a key, a tool (e.g., torque wrench), a code (e.g., combination) or without a tool. In another non-limiting example, the lead connector 130 may minimize or eliminate damages or changes to the lead's structure, enabling the lead to remain sufficiently intact to generally reduce the risk of the lead fracturing or breaking and enable current flow through the entire lead.

Figure 13:
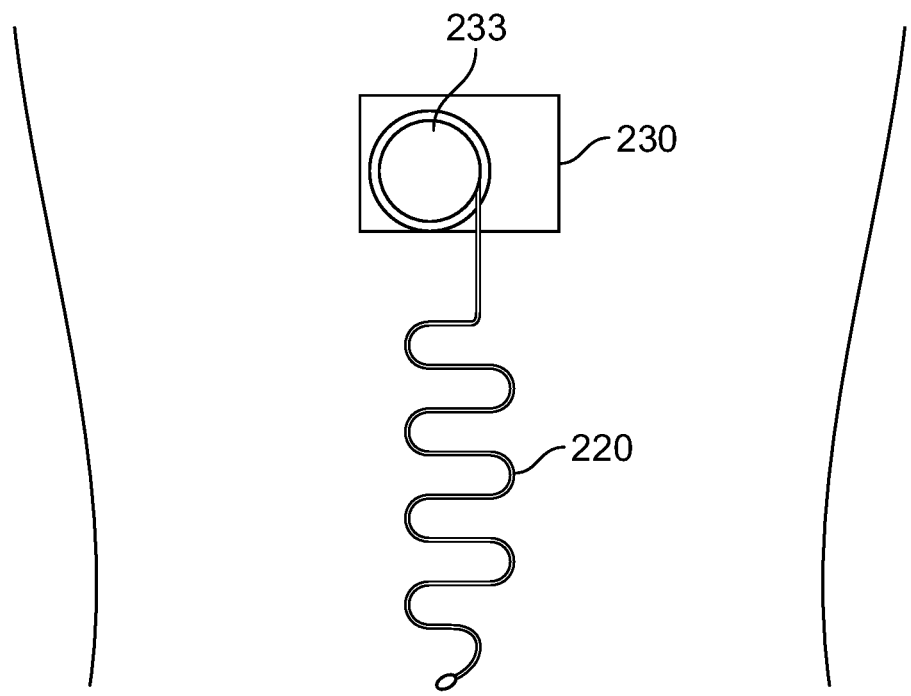
FIG. 13 are schematic views of embodiments of a lead connector with lead storage mechanism.
Figure 13:
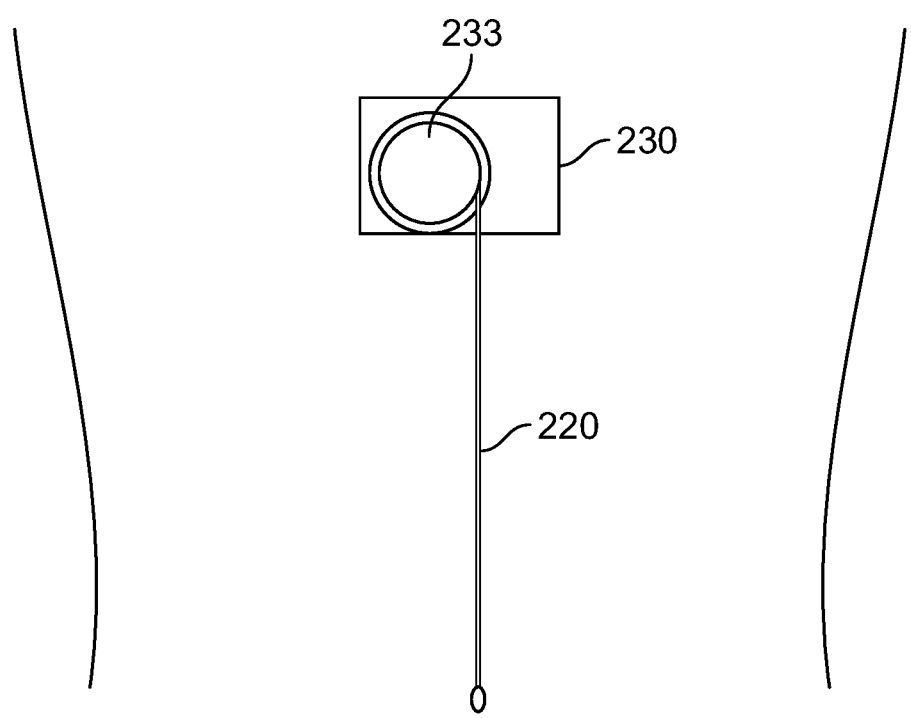
Figure 14:
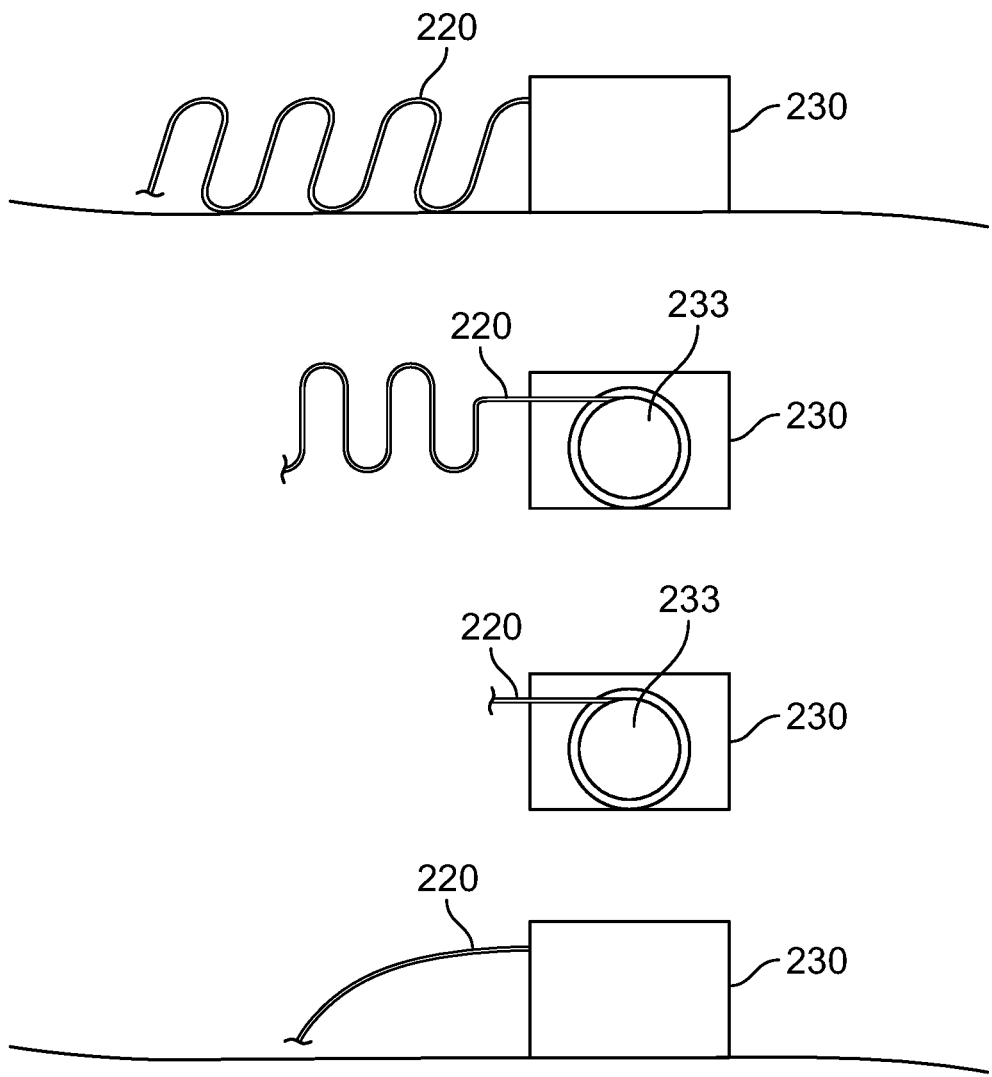
FIG. 14 are schematic views of embodiments of a lead connector with lead storage mechanism.

A lead connector 230 may include a lead storage mechanism 233 to store a lead 220 (e.g., while the lead is coupled to the lead connector 230). This mechanism may reduce the excess length of lead 220 between the lead connector 230 and the point from which the lead 220 exits the body. This may reduce the risk of the lead 220 being caught on an object and being pulled and/or breaking. If the lead 220 is caught, for example, on an external object or from a body part, then the excess lead 220 stored on the mechanism may be released rather than dislodging or moving the lead 220 from the tissue, fracturing the lead 220 (inside or outside the body), and/or pulling the lead 220 out and decoupling from the lead connector 230. In a non-limiting example, the mechanism 233 may be a spool around which the lead 220 is wound, either manually or automatically (e.g., using a spring). In another non-limiting example, the mechanism 233 may be located on the outside of the lead connector 230 or within the lead connector 230—See FIGS. 13 and 14. In addition, the lead connector 230 may be padded on one or more sides to provide comfort while wearing the lead connector 230.

Figure 15:
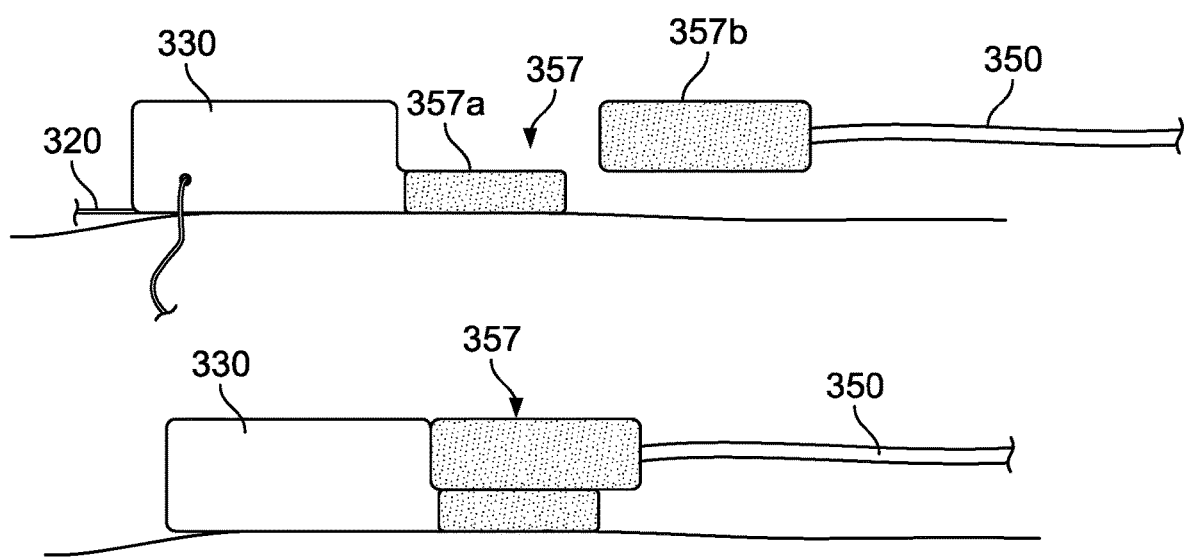
FIG. 15 are schematic views of embodiments of a lead connector.
Figure 16:
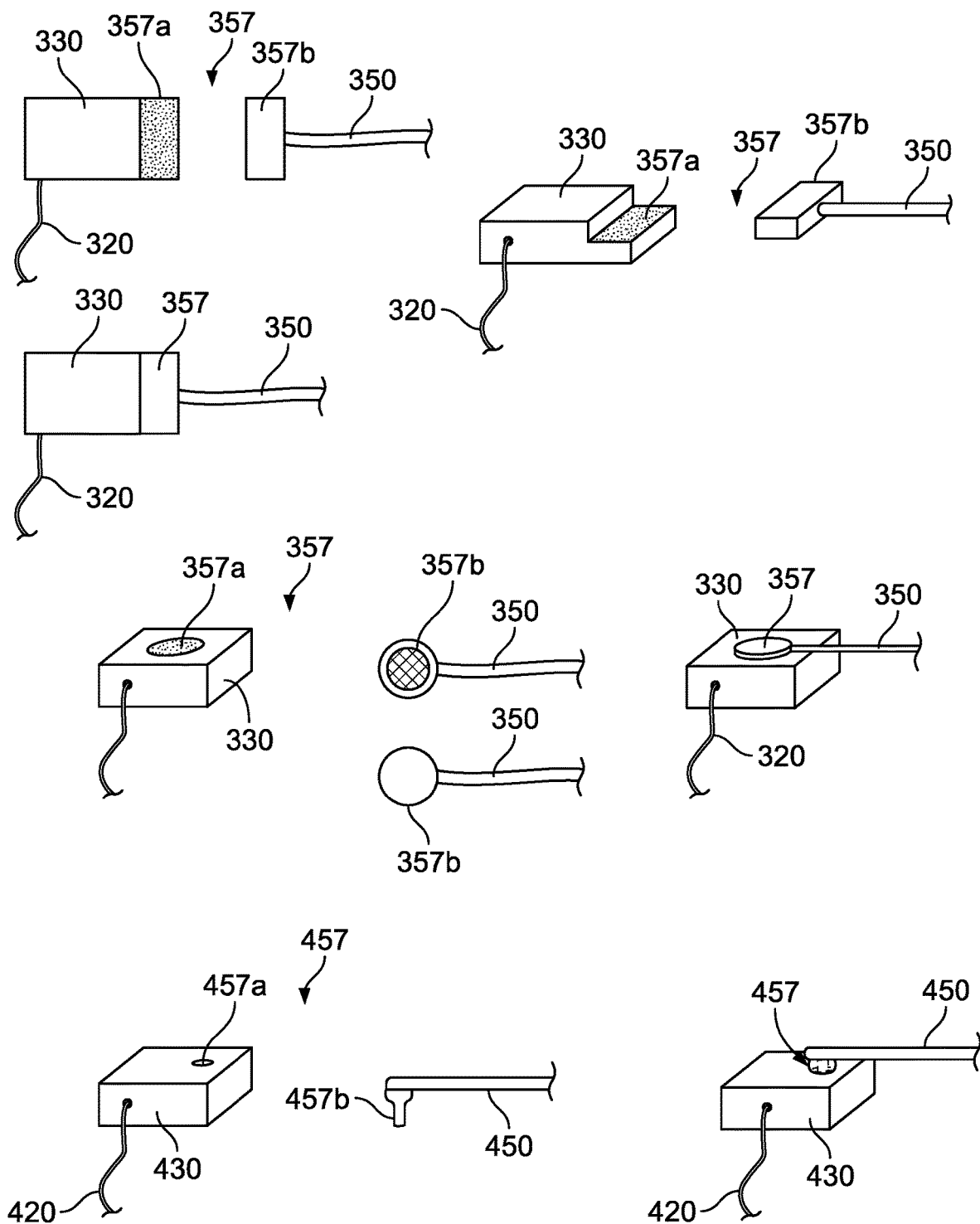
FIG. 16 are schematic views of embodiments of a lead connector.

A lead connector 330 may be designed to couple to the stimulator pod 40 easily, and may enable connection using a single hand. In a non-limiting example, the lead connector 330 may be connected to the stimulator pod 40 via a patient cable 350. In a non-limiting example, the patient cable 350 may connect to the lead connector 330 through a connection 357, such as by way of a non-limiting example a magnetic connection. It should be understood, however, that while a magnetic connection is described, the connection may be any mechanical connection in addition to or alternatively to the magnetic connection. The connection 357 may be oriented at various angles with respect to the surface of the skin. In a non-limiting example, the connection 357 is oriented generally perpendicular to the skin. In another non-limiting example, the connection 357 is generally parallel to the surface of the skin. In yet another embodiment, the connection 357 may be easy for the user to make (e.g., does not require great dexterity, may be connected even without looking at the connectors) and strong enough to prevent inadvertent disconnection (e.g., due to common body movements or small forces, etc.) while disconnecting when subjected to stronger forces that may dislodge the lead (e.g., from external objects or body parts pulling or tugging on the lead connector or stimulator attached to the lead connector). The connection 357 may prevent the lead 320 from dislodging or fracturing by disconnecting the lead connector 330 and cable when the patient cable 350 is pulled rather than transmitting the force along the lead 320—See FIGS. 15 and 16. In some embodiments, the connector 357 may include two portions a positive 357a and negative 357b portion of a magnet that attract to one another at a predetermine force. It should be understood that the positive portion may be on either side 357a or 357b and the negative portion may be on either side 357a and 357b. Further still one portion may be a magnet (357a or 357b) and the other side may be a material attracted by the magnet (357a or 357b). In a non-limiting example, the magnetic connectors 330 may be structured such that the surrounding magnetic field is reduced and avoids interfering with objects placed near the magnetic connectors (e.g., credit cards, cell phones).

Further still, the lead 320 may connect directly to the stimulator pod 40 (i.e., lead connector may be built into or integrally with the stimulator pod). The stimulator pod may be placed directly over or adjacent to the lead exit site to protect the exit site. There may be a clear window through which the lead exit site can be monitored for safety (e.g., infections, irritation).

In another non-limiting example, the patient cable 450 may connect to the lead connector 430 using a jack 457b and plug 457a, and the jack 457b may be located on the patient cable 450 and oriented at an angle (such as 90 degrees) to the patient cable 450. This jack 457b may be connected to the plug 457a on the lead connector 430 using a downward force, enabling connection using a single hand. The very small distances between the magnetic armature of the plug 457a and the permanent magnet structure of the lead connector 430 means that the residual field outside the lead connector 430 is very small—see FIG. 16.

Figure 17:
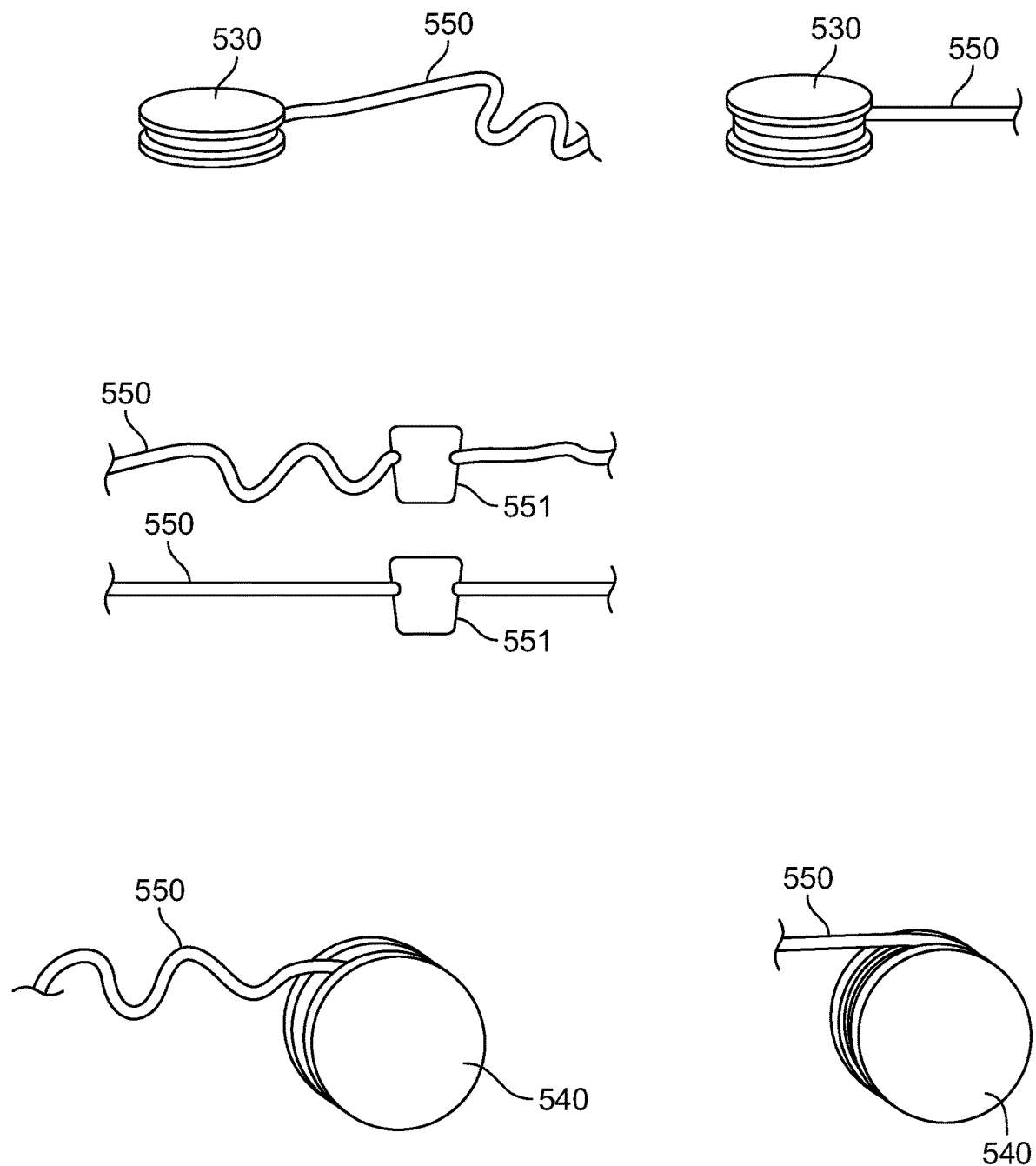
FIG. 17 are schematic views of embodiments of a lead connector with a storage device.

As shown in FIG. 17, a patient cable 550 may attach to the stimulator and stored or organized (e.g., wound, coiled, wrapped around) to reduce the length of the patient cable 550 (or lead 520) that may become caught, for example, on an external object or a body part. In a non-limiting example, the excess patient cable 550 may be stored in a storage device 551 attached to the cable 550, on the lead connector 530, and/or on the stimulator pod 540. In a non-limiting example, the storage device 551 is a spool around which the patient cable 550 may be wound manually or automatically (e.g., via a spring). In an embodiment, the patient cable 550 may be coiled or wound around a spool on the stimulator pod 540, and forces on the patient cable 550 cause the patient cable 550 to be uncoiled from the spool rather than disconnect from the stimulator pod 540, transmit the force to the lead connector 530, and/or patient cable 550—See FIG. 17.

The stimulation system may contain patient cable that attach to the stimulator pod available in multiple lengths. In a non-limiting example, the patient cable with the shortest length that enables connection between the stimulator pod and the lead connector may be selected to reduce the risk of the patient cable catching on an object or body part and disconnecting the system, dislodge the lead, and/or fracture the lead.

Figure 18:
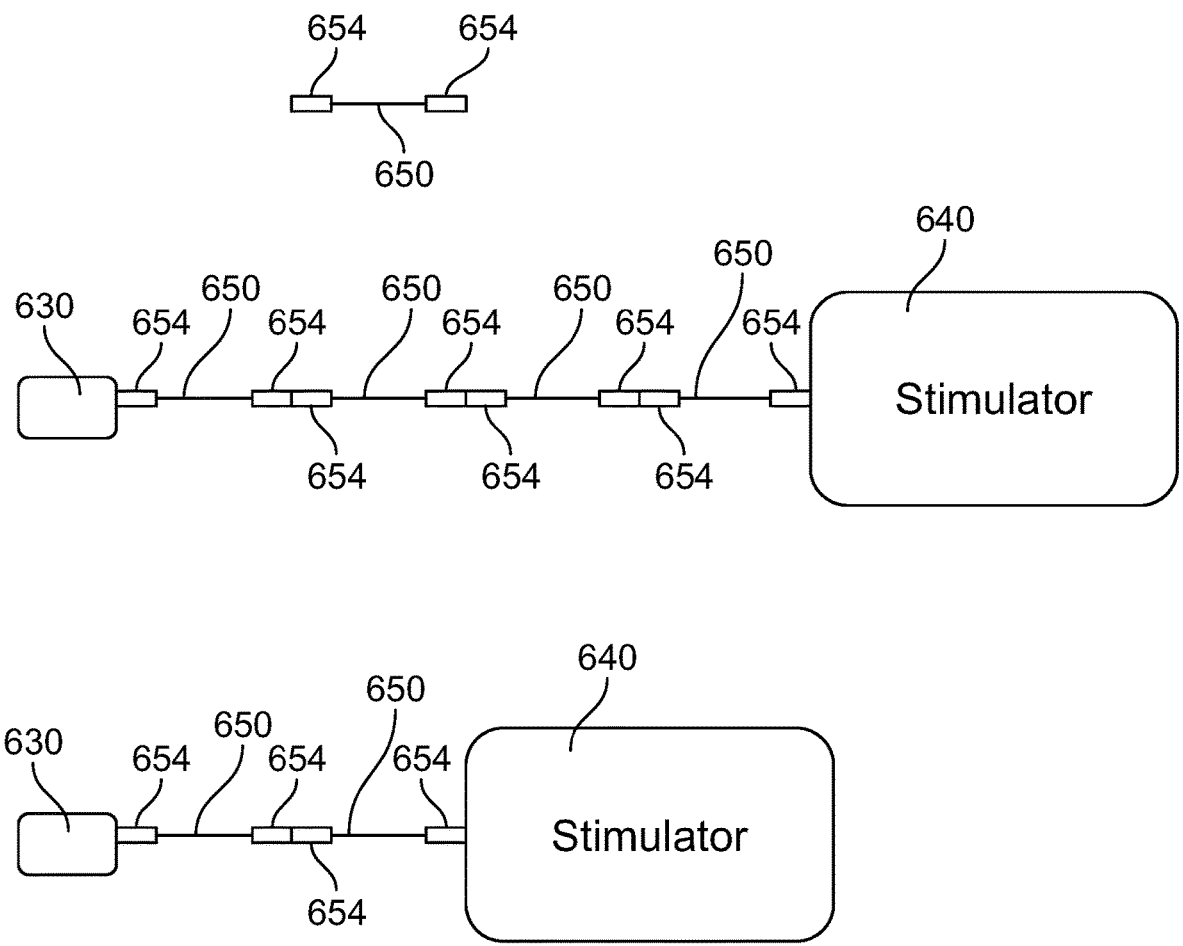
FIG. 18 are schematic view of embodiments of the lead connector and stimulator pod with patient cables with breakaway mechanisms.

As shown in FIG. 18, two or more patient cable 650 may be used to connect the stimulator pod 640 to the lead connector 630. The use of more than one patient cable 650 to connect to the stimulator pod 640 may enable more control of the total length of cabling between the lead connector 630 and stimulator pod 640 (e.g., compared to the use of a single cable with a fixed length). In a non-limiting example, each individual patient cable 650 may be short (e.g., <1-2 inches), which may enable more precise control over the total length of the multiple cables connected together. In another non-limiting example, patient cables 650 may be available in different lengths. In a non-limiting example, multiple patient cable 650 may be connected together, and the minimum number of cables are used to connect the lead connector 630 to the stimulator pod 640 to minimize the total length of cable, thus reducing the risk of the cables catching or snagging (e.g., on an external object or a body part)—See FIG. 17. Each of the patient cables 650 may be attached utilizing a breakaway mechanism 654 of any configuration, such as that described above. Each patient cable 650 may include a breakaway mechanism 654 attached to each end thereof. The breakaway mechanism 654 may connect to one another and/or the lead connector 630 and/or the stimulator pod 640 such that they remain connected upon applicable of a predetermined force. If the force applied exceeds this predetermined force any of or a plurality of the breakaway connectors 654 may become disconnected. This prevents the electrode from moving from within the patient. The breakaway connectors 654 may also be easy to attach once they have become disconnected. The breakaway connector 654 may utilize magnets, bayonet attachment, biasing force, friction fit, etc. to connect together. Any appropriate configuration may be utilized.

In some embodiments, the stimulator pod may enable coordinated stimulation across two or more stimulator pods. In the alternative or in addition, the controller pod and/or programmer unit may enable coordinated stimulation across two or more stimulator pods. Coordinated stimulation may enable stimulation across multiple stimulator pods to start and stop in a coordinated manner to avoid asynchronous activation of muscle on opposite sides of the body (e.g., the back or torso), which may cause loss of balance or discomfort. Control over stimulation across multiple stimulator pods may also prevent synchronized stimulation, for example, to avoid activation of opposing muscles (e.g., biceps and triceps), which may cause discomfort. In a non-limiting example, one of the stimulator pods, controller pod and/or programmer unit may communicate with other stimulator pods directly. In another non-limiting example, each stimulator pods may be connected to a central controlling unit, which may be another stimulator pod or may be a non-stimulating control unit. In a non-limiting example, communication among stimulator pods and/or control units (controller pod or programmer unit) may be wireless (e.g., via Bluetooth, WI-Fi) or wired (e.g., cables).

The stimulator pod may provide simple programming of stimulation intensity by controlling stimulation amplitude and pulse duration with a single programmable parameter for intensity. Stimulation intensity is determined by multiple parameters, including (but not limited to) stimulation amplitude and pulse duration. For example, stimulation intensity may be increased by increasing stimulation amplitude, pulse duration, or a combination of the two. Controlling multiple parameters such as stimulation amplitude and pulse duration using a single parameter may reduce the complexity of the procedure to program stimulation parameters by reducing the number of parameters that can be changed from 2 or more to 1. As a non-limiting example, the minimum of the stimulation intensity parameter (e.g., 0) may set the stimulation amplitude and pulse duration to their lowest values (e.g., 0.2 mA and 10 microseconds). As another non-limiting example, increasing the stimulation intensity parameter may change the stimulation amplitude, the pulse duration, or both.

Figure 19:
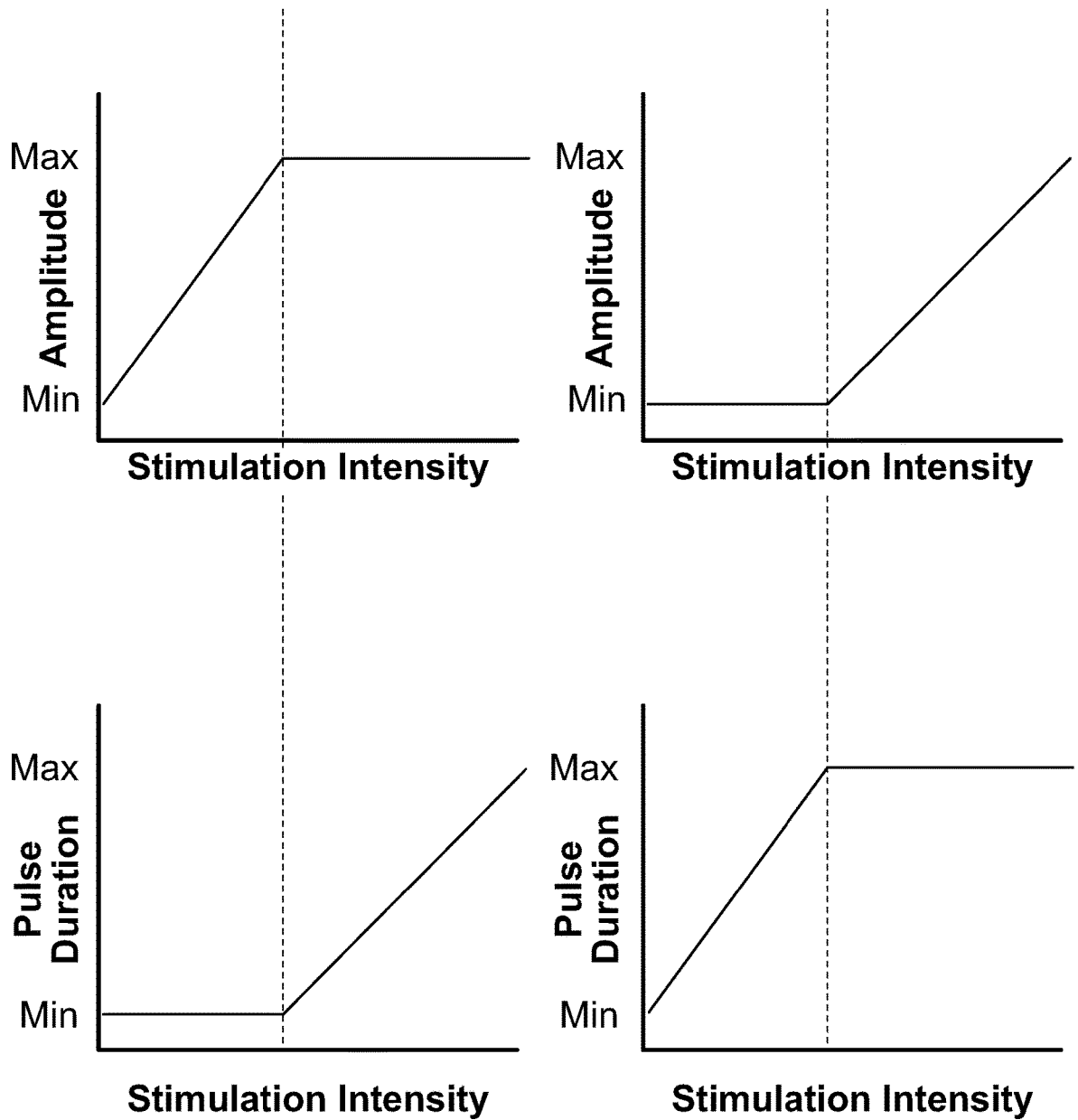
FIG. 19 are graphical representations of stimulation intensity with amplitude and pulse duration.

In yet another embodiment, increasing the stimulation intensity parameter from the minimum value may first increase the stimulation amplitude while keeping the pulse duration at a minimum until the maximum value of the stimulation amplitude (e.g., 20-30 mA) is reached. Then, continuing to increase the stimulation intensity parameter may keep the stimulation amplitude fixed at the maximum value while increasing the pulse duration until the maximum value of the pulse duration is reached. In these embodiments, stimulation intensity is simple to program and may be increased while keeping pulse duration as low as possible. This keeps the stimulation charge required to activate nerve fibers as low as possible and increases the ability to selectivity stimulation large diameter fibers over small diameter fibers. In another non-limiting example, increasing the stimulation intensity parameter from the minimum value may first increase the stimulation amplitude while keeping stimulation amplitude at a minimum. Then, continuing to increase the stimulation intensity parameter beyond the maximum value of pulse duration (e.g., 200 microseconds) may keep the pulse duration fixed at the maximum value while increasing the amplitude until the maximum value of the stimulation amplitude is reached. In this example, stimulation intensity increases while keeping stimulation amplitude as low as possible, which keeps the power consumption of the pulse as low as possible for a given charge per pulse. Left column of FIG. 19 is the first example given, keeping pulse duration low. The right column of FIG. 19 is the second example, keeping stimulation amplitude low.

In another non-limiting example, a lead connector may be attached to the lead prior to or after insertion of an introducer system, enabling stimulation through the lead tip during the lead placement procedure. In one embodiment, the connector may be attached to the lead by dropping the lead into a slot or hole on the block and closing a flap which implements an insulation displacement connection (e.g., cutting through the insulative material aside to form a connection with the conductive lead wire). This lead connector may improve the speed and ease of lead connection because it can be attached without the use of tools (e.g., no wire cutters, scissors, and screwdrivers). For example, in this embodiment, the lead may be placed into a slot in a lead connector block and secured using a lockable, reversible one-handed mechanism to displace the insulation on the lead body. The insulation displacement mechanism inside the lead connector may also cut the lead distal to the electrical connection. Once the connection has been made and the excess lead is trimmed, a lock (e.g., sliding, twisting, button press) may ensure that the flap on the block cannot be reopened accidentally. This feature prevents loss of connection between the lead connector and lead, which would result in loss of therapeutic benefit. The lead connector may mate with another lead connector (e.g., patient cable or plug to the stimulator pod) to complete the circuit from the stimulator pod to the lead tip electrode.

In one embodiment, the connection between the two lead connectors may be magnetic. In this case, the shape of the lead connectors will prevent improper alignment of the lead connector (e.g., lead connectors that only fit together in one orientation). The magnetic connection may be used for both temporary and permanent stimulation delivery (e.g., during lead placement procedure or during patient's home use of the therapy). After obtaining proper lead placement location, the lead connector block may be removed and replaced following removal of the introducer system needle(s) and sheath(s). In one embodiment, the connection may be deactivated by pressing or sliding open the slot that contains the lead. In this example, the lead connector block may be removed or cut off prior to removal of the introducer and then quickly re-attached to a more proximal location on the lead. Following removal of the introducer, the lead may be placed in the slot and connected with a one-touch mechanism (e.g., pressing, sliding) and then the lead connector may be attached to the stimulator cable.

The magnetic connection may act as a quick-release connection that will prevent accidental lead (or electrode) dislodgement due to a pulled lead and/or patient cable. Instead of transferring force to the lead exit site and lead, any forces on the patient cable will be discharged due to the breaking of the magnetic connection between the patient cable and lead connector block. If desired by the clinician, a permanent connection may be made by locking the two-connector pieces together using a press button lock (or any other suitable lock). In addition to mating with the lead connector block, in another embodiment, the magnetic cable connector for the stimulator pod may also mate with an identical version of the lead connector block, which is connected to the test stimulator via a cable. In another embodiment, the magnetic cable connector originating from the stimulator pod may be bifurcated to connect with multiple lead connector blocks (e.g., to enable stimulation of two leads with one stimulator).

A battery-operated, body-worn stimulator pod may generate electrical current that may be administered via the lead and/or introducer. In one embodiment, the stimulator pod is a small pod (e.g., with rounded contours and of minimal profile height) that is worn on the body via a gel patch electrode that serves as the return electrode and is connected with two snaps that also provide electrical connection. In one embodiment, the stimulating pod has a minimal user interfaces (e.g., a press button start/stop, LED lights and a speaker or buzzer) to provide critical feedback to the patient. For example, the lights may blink or light up (e.g., different colors or different flashing patterns) if the battery is low or if there is a problem with stimulation. This important feedback will alert the patient or clinician to address any issues, such as battery failure, gel pad detachment, or open connection. In the non-limiting example with a magnetic lead connector, it is important that the stimulator pod produces an alert if the quick-release cable is accidentally dislodged without the patient's knowledge. Additionally, lead errors that cause stimulation to stop due to, for example, high electrode impedance issues (e.g., due to lost connection between skin and return electrode), and can impact therapy usage time and therapeutic benefit received by the patient and the audible or visible alert of the stimulating pod prevents this. Further, in one embodiment, the stimulator memory will generate an activity log for documenting usage of the stimulator and errors during therapy. The stimulator log may include a list of errors that occurred, along with timestamps of the time that errors occurred, a history of usage time, including amplitude and stimulation parameter settings used. These features are important to ensure that patients are able to effectively use the stimulation and that clinicians can effectively monitor their stimulation usage.

Figure 20:
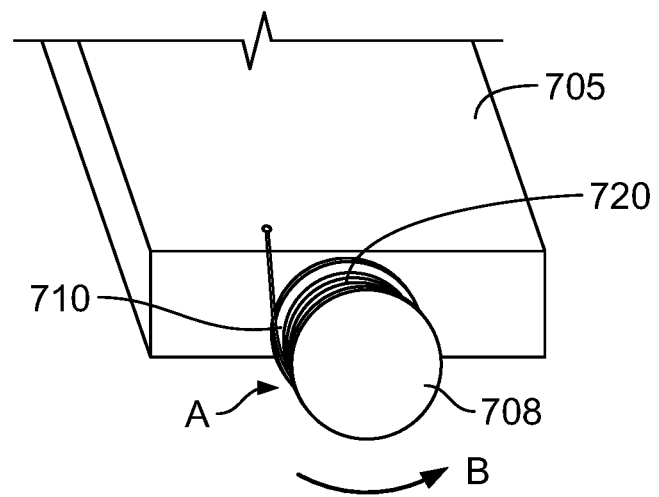
FIG. 20 is a perspective view of embodiments of an IDC.
Figure 21:
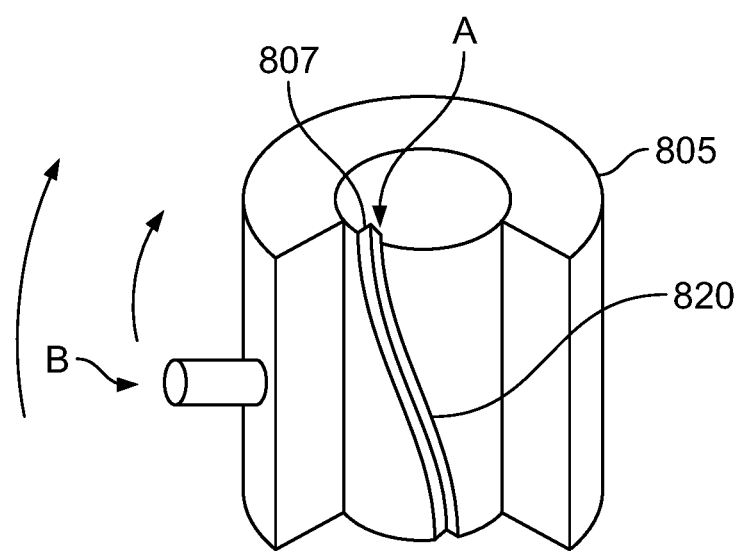
FIG. 21 is a perspective view of embodiments of an IDC.

Exemplary embodiments of the IDC are depicted in FIGS. 20 and 21. An IDC 705 shown in FIG. 20 may include a drawer type mechanism or disc 708 that is insertable into the body of the IDC 705 and removable therefrom. A slot 710 of any appropriate shape and size to firmly hold or engage the lead 720 may be positioned within the disc 708. A user may push the disc 708 to rotate such and move the lead 720 fully inside the IDC 705. The IDC may be integral with or attached to the lead connector. Barbs (not shown) may be included in the interior of the IDC 705 if necessary to remove insulation from the lead 720 to expose the underlying wire.

In another embodiment shown in FIG. 21, an IDC 805 may have a generally cylindrical shape. The IDC may include an aperture, slot or opening 807 into which the lead 820 may be inserted. The IDC may include an actuating lever to rotate the IDC until the lead 720 is fully inside the IDC. Barbs (not shown) may be included in the interior of the IDC 805 if necessary to remove insulation from the lead 820 to expose the underlying wire.

Figure 22:
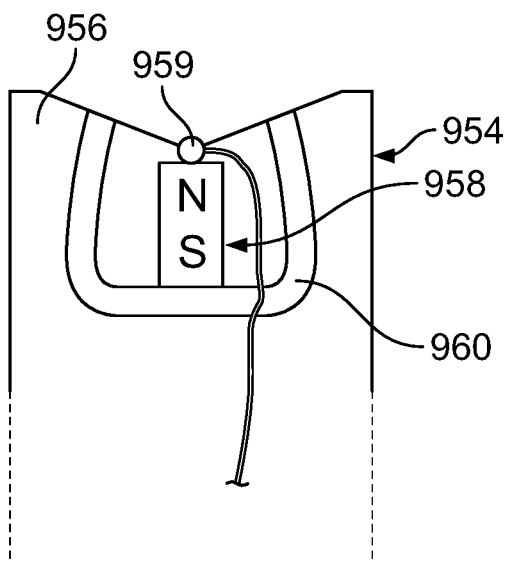
FIG. 22 is a cross-sectional view of a portion of a breakaway mechanism.
Figure 23:
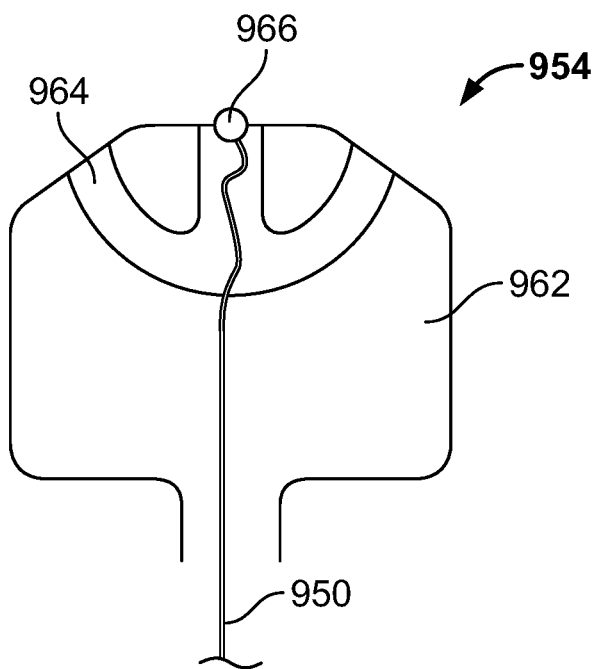
FIG. 23 is a cross-sectional view of a portion of a breakaway mechanism.

An additional embodiment of a breakaway mechanism 954 is shown in FIGS. 22-25. In FIG. 22, a portion of the breakaway mechanism 954 is shown as a receptacle portion 956. The receptacle portion 956 may include a magnet 958 of any appropriate embodiment that includes a contact point 959. The receptacle portion 956 may include an iron magnetic stator 960, which may act as a pathway keeper. FIG. 23 depicts a mating portion of the breakaway mechanism 954, which is a plug 962. The plug 962 may include an iron magnetic keeper path 964 and a contact 966. The patient cable 950 may be operatively attached with the plug 962.

Figure 24:
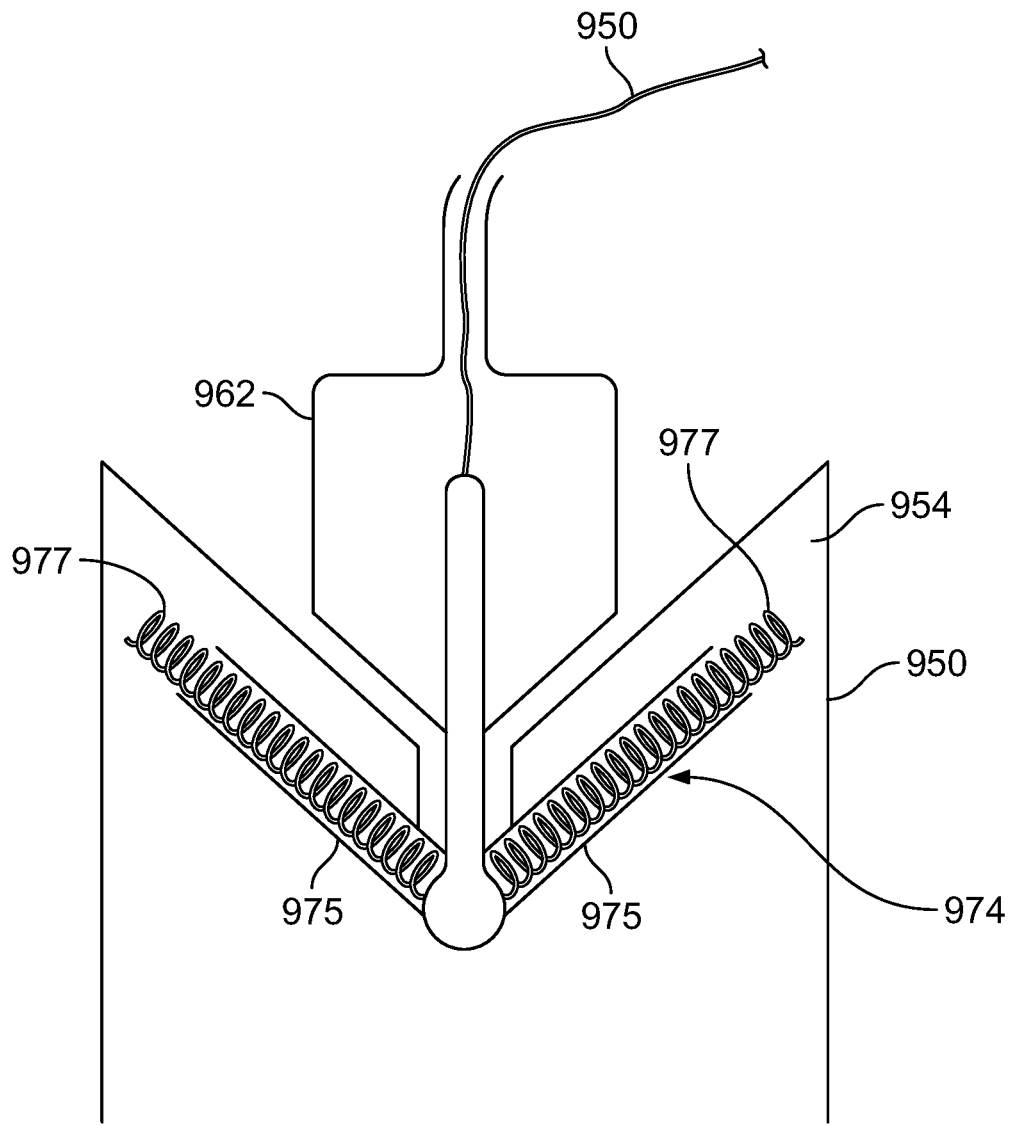
FIG. 24 is a cross-sectional view of a breakaway mechanism.
Figure 25:
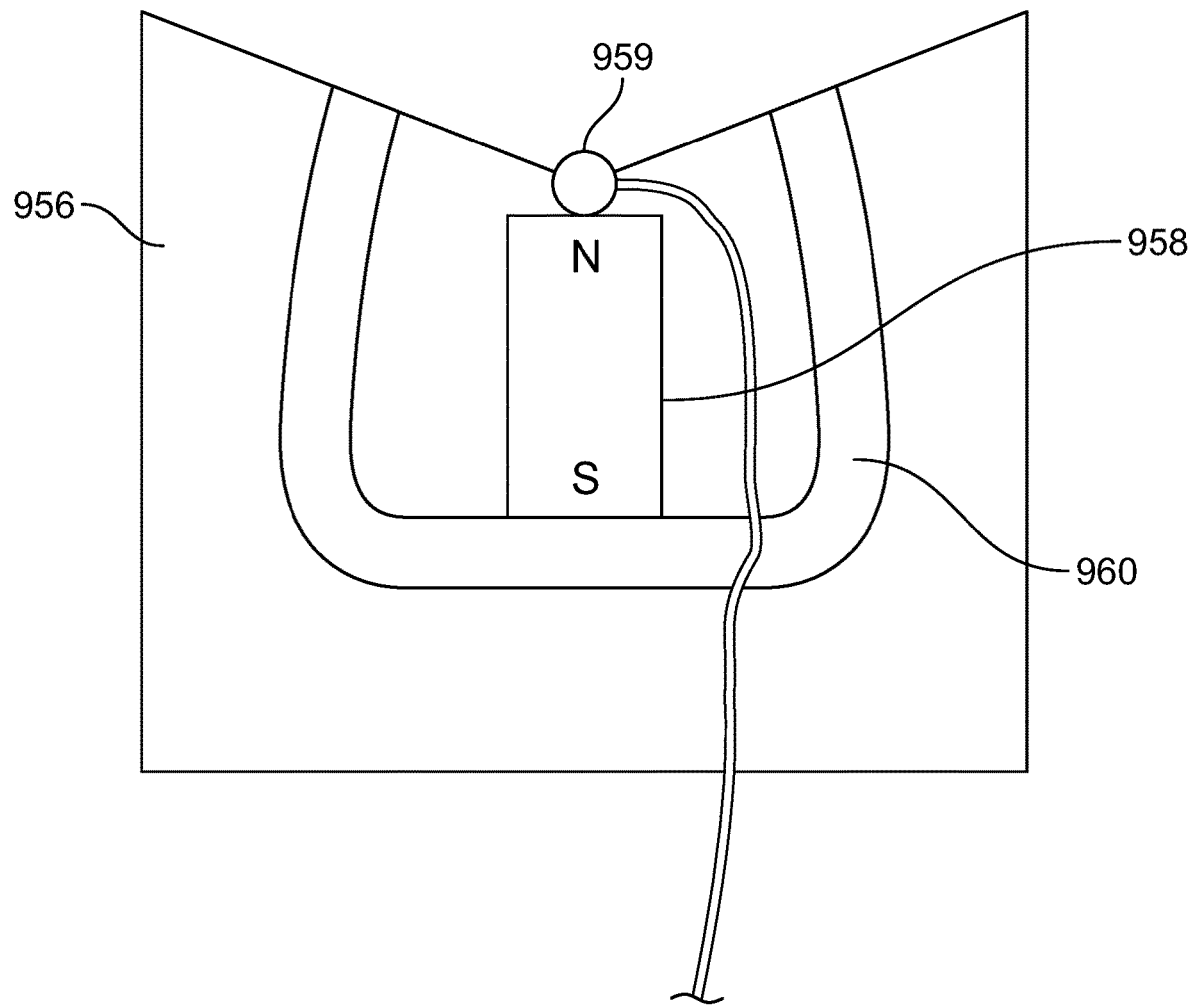
FIG. 25 is a cross-sectional view of a portion of a breakaway mechanism.

As shown in FIG. 24, the breakaway mechanism 954 may include a spring loaded plunger mechanism 974. The plunger mechanism 974 utilizes a pair of biasing member 977 that may push plungers 975 toward each other as the plug 962 is inserted into the receptacle 956. This may secure the breakaway mechanism 954 together. The force utilized to keep the breakaway mechanism 954 together is defined such that any amount of force applied to the system that exceeds such force will cause the plug 962 to separate from the receptacle 956, e.g., if there is a force applied to the patient cable 950 because it snags on something. This will generally protect the system. In particular, it generally prevents the lead and/or electrode from becoming disengaged or moved from their intended position.

Although the embodiments of the present teachings have been illustrated in the accompanying drawings and described in the foregoing detailed description, it is to be understood that the present teachings are not to be limited to just the embodiments disclosed, but that the present teachings described herein is capable of numerous rearrangements, modifications and substitutions without departing from the scope of the claims hereafter.

We claim:

1. An electrical stimulation system comprising:
   a lead connector comprising a lead body having at least one slot or channel and a contact element proximate to at least portion of the slot or channel;
   a coiled lead inserted into said slot or channel, wherein the contact element establishes an electrical connection with the coiled lead and wherein the coiled lead has an engagement force when inserted into a body of a patient;
   a patient cable selectively attachable to the lead body, wherein the contact element establishes an electrical connection with the patient cable; and
   wherein the lead connector further comprises a breakaway mechanism configured to selectively disconnect the patient cable from the lead body upon application of a force exceeding a predetermined force, wherein the predetermined force is less than the engagement force.

2. The electrical stimulation system of claim 1 further comprising an electrical stimulator operatively attached with the patient cable, wherein the electrical stimulator is configured to apply electrical stimulation.

3. The electrical stimulation system of claim 2, wherein the contact element includes micro-structured barbs to engage the coiled lead.

4. The electrical stimulation system of claim 2, wherein the breakaway mechanism comprises a Velcro-style, hook and loop attachment.

5. The electrical stimulation system of claim 2, wherein the breakaway mechanism comprises a neodymium magnet.

6. The electrical stimulation system of claim 2, wherein the breakaway mechanism comprises at least one of: a rare earth magnet, a samarium cobalt magnet, an alnico magnet, a ceramic magnet, and a ferrite magnet.

7. The electrical stimulation system of claim 2 further comprising an insulation displacement device proximate to the slot or channel, said insulation displacement device engaging the coiled lead to remove any electrical insulation therefrom as or after the coiled lead is inserted into the slot or channel.

8. The electrical stimulation system of claim 7, wherein the contact element comprises micro-structured barbs to temporarily engage the percutaneous coiled lead as or before electrical insulation is removed from the percutaneous coiled lead.

9. The electrical stimulation system of claim 2, wherein a spring-loaded, conductive pin carried on the patient cable engages a mating element formed on the lead body, said engagement of the mating element with the patient cable creating an electrical connection between the coiled lead and the patient cable by way of the contact element.

10. The electrical stimulation system of claim 2, wherein a spring-loaded, conductive pin formed on an exterior facing of the lead body engages a mating element formed on the patient cable, the engagement of the pin with the patient cable creating an electrical connection between the coiled lead and the patient cable by way of the contact element.

11. The electrical stimulation system of claim 2 further comprising an adhesive bandage mated to the lead body wherein a profile of the lead body is even with or below a thickness of the adhesive bandage.

12. The electrical stimulation system of claim 2, wherein the lead body includes a connection point for attachment to the patient cable.

13. The electrical stimulation system of claim 12, wherein the connection point has an inverted Y shape.

14. The electrical stimulation system of claim 12, wherein the connection point has a plurality of movable arms.

15. The electrical stimulation system of claim 12, wherein the connection point has a biasing fitting.

16. The electrical stimulation system of claim 2, wherein the lead connector comprises a rotating element engageable with the coiled lead, the rotating element configured to adjust the engagement force.

17. The electrical stimulation system of claim 16, wherein the rotating element comprises at least of a knob, dial, spool or post.

18. The electrical system of claim 2, wherein the lead connector is bifurcated into multiple divisions to receive a plurality of coiled leads.

19. The electrical system of claim 18 further comprising a plurality of coiled leads.

20. The electrical system of claim 19, wherein the lead connector comprises a lead storage mechanism, wherein the lead storage mechanism reduces a length of the coiled lead extending from the lead connector.

21. The electrical system of claim 20, wherein the lead storage mechanism comprises a spool.

22. The electrical stimulation system of claim 1, wherein the lead body includes a releasable force fitting comprising a groove or indentation.

* * * * *